US008353932B2

(12) United States Patent
Jackson

(10) Patent No.: US 8,353,932 B2
(45) Date of Patent: Jan. 15, 2013

(54) POLYAXIAL BONE ANCHOR ASSEMBLY WITH ONE-PIECE CLOSURE, PRESSURE INSERT AND PLASTIC ELONGATE MEMBER

(76) Inventor: Roger P. Jackson, Prairie Village, KS (US)

( * ) Notice: Subject to any disclaimer, the term of this patent is extended or adjusted under 35 U.S.C. 154(b) by 686 days.

(21) Appl. No.: 12/229,207

(22) Filed: Aug. 20, 2008

(65) Prior Publication Data

US 2008/0319490 A1   Dec. 25, 2008

Related U.S. Application Data

(63) Continuation-in-part of application No. 11/894,001, filed on Aug. 17, 2007, now Pat. No. 8,292,926, and a continuation-in-part of application No. 11/522,503, filed on Sep. 14, 2006, now Pat. No. 7,766,915, and a continuation-in-part of application No. 12/008,067, filed on Jan. 8, 2008.

(60) Provisional application No. 60/994,083, filed on Sep. 17, 2007, provisional application No. 60/851,353, filed on Oct. 12, 2006, provisional application No. 60/905,472, filed on Mar. 7, 2007, provisional application No. 60/722,300, filed on Sep. 30, 2005, provisional application No. 60/725,445, filed on Oct. 11, 2005, provisional application No. 60/728,912, filed on Oct. 21, 2005, provisional application No. 60/736,112, filed on Nov. 10, 2005, provisional application No. 60/832,644, filed on Jul. 21, 2006, provisional application No. 60/897,723, filed on Jan. 26, 2007.

(51) Int. Cl.
*A61B 17/70* (2006.01)
(52) U.S. Cl. ...................................... 606/246
(58) Field of Classification Search .......... 606/246, 606/250–261, 263, 265–272, 279, 65, 287, 606/262, 264
See application file for complete search history.

(56) References Cited

U.S. PATENT DOCUMENTS

| 854,956 A | 5/1907 | Martin |
| 2,243,717 A | 5/1941 | Moreira |
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |

(Continued)

FOREIGN PATENT DOCUMENTS

CA   2577436   6/2006

(Continued)

OTHER PUBLICATIONS

*EBI Omega 21* Brochure, EBI Spine Systems, pub. 1999.
*Claris Instrumentation* Brochure, G Med, pub. 1997.
*CD Horizon M8 Multi Axial Screw Spinal System* Brochure, Medtronic Sofamor Danek, no publish date.
*Contour Spinal System* Brochure, Ortho Development, no publish date.

(Continued)

*Primary Examiner* — Alvin J. Stewart
(74) *Attorney, Agent, or Firm* — John C. McMahon

(57) ABSTRACT

A medical implant assembly includes a polyaxial bone anchor having a shank, a receiver, a lower compression insert with planar surfaces for closely receiving an elongate connecting member with planar surfaces and a one-piece closure structure. The connecting member is made from a polymer. The closure structure engages both the connecting member and the insert with the engagement between the closure structure and the insert securely locking the polyaxial mechanism even if the connecting member exhibits creep.

32 Claims, 6 Drawing Sheets

U.S. PATENT DOCUMENTS

| | | | |
|---|---|---|---|
| 4,033,139 A | 7/1977 | Frederick | |
| 4,041,939 A | 8/1977 | Hall | |
| 4,190,091 A | 2/1980 | Colognori | |
| 4,373,754 A | 2/1983 | Bollfrass et al. | |
| 4,448,191 A | 5/1984 | Rodnyansky et al. | |
| 4,484,570 A | 11/1984 | Sutter et al. | |
| 4,600,224 A | 7/1986 | Blose | |
| 4,653,486 A | 3/1987 | Coker | |
| 4,703,954 A | 11/1987 | Ortloff et al. | |
| 4,707,001 A | 11/1987 | Johnson | |
| 4,743,260 A | 5/1988 | Burton | |
| 4,748,260 A | 5/1988 | Marlett | |
| 4,759,672 A | 7/1988 | Nilsen et al. | |
| 4,790,297 A | 12/1988 | Luque | |
| 4,836,196 A | 6/1989 | Park et al. | |
| 4,877,020 A | 10/1989 | Vich | |
| 4,887,596 A | 12/1989 | Sherman | |
| 4,946,458 A | 8/1990 | Harms et al. | |
| 4,950,269 A | 8/1990 | Gaines, Jr. | |
| 5,005,562 A | 4/1991 | Cotrel | |
| 5,019,080 A | 5/1991 | Hemer | |
| 5,020,519 A | 6/1991 | Hayes et al. | |
| 5,022,791 A | 6/1991 | Isler | |
| 5,034,011 A | 7/1991 | Howland | |
| 5,067,955 A | 11/1991 | Cotrel | |
| 5,084,048 A | 1/1992 | Jacob et al. | |
| 5,092,635 A | 3/1992 | DeLange et al. | |
| 5,092,866 A | 3/1992 | Breard et al. | |
| 5,102,412 A | 4/1992 | Rogozinski | |
| 5,129,388 A | 7/1992 | Vignaud et al. | |
| 5,147,363 A | 9/1992 | Harle | |
| 5,154,719 A | 10/1992 | Cotrel | |
| 5,176,483 A | 1/1993 | Baumann et al. | |
| 5,176,678 A | 1/1993 | Tsou | |
| 5,176,680 A | 1/1993 | Vignaud et al. | |
| 5,180,393 A | 1/1993 | Commarmond | |
| 5,207,678 A | 5/1993 | Harms et al. | |
| 5,217,497 A | 6/1993 | Mehdian | |
| 5,257,993 A | 11/1993 | Asher et al. | |
| 5,261,907 A | 11/1993 | Vignaud et al. | |
| 5,261,912 A | 11/1993 | Frigg | |
| 5,275,601 A | 1/1994 | Gogolewski et al. | |
| 5,282,862 A | 2/1994 | Baker et al. | |
| 5,282,863 A * | 2/1994 | Burton | 606/254 |
| D346,217 S | 4/1994 | Sparker et al. | |
| 5,306,275 A | 4/1994 | Bryan | |
| 5,312,404 A | 5/1994 | Asher et al. | |
| 5,321,901 A | 6/1994 | Kelly | |
| 5,330,472 A | 7/1994 | Metz-Stavenhagen | |
| 5,346,493 A | 9/1994 | Stahurski et al. | |
| 5,358,289 A | 10/1994 | Banker et al. | |
| 5,360,431 A | 11/1994 | Puno et al. | |
| 5,375,823 A | 12/1994 | Navas | |
| 5,385,583 A | 1/1995 | Cotrel | |
| 5,395,371 A | 3/1995 | Miller et al. | |
| 5,409,489 A | 4/1995 | Sioufi | |
| 5,414,661 A | 5/1995 | Ihara | |
| 5,415,661 A | 5/1995 | Holmes | |
| 5,423,816 A | 6/1995 | Lin | |
| 5,427,418 A | 6/1995 | Watts | |
| 5,429,639 A | 7/1995 | Judet | |
| 5,443,467 A * | 8/1995 | Biedermann et al. | 606/65 |
| 5,466,237 A | 11/1995 | Byrd, III et al. | |
| 5,468,241 A | 11/1995 | Metz-Stavenhagen et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,484,437 A | 1/1996 | Michelson | |
| 5,484,440 A | 1/1996 | Allard | |
| 5,487,742 A | 1/1996 | Cotrel | |
| 5,489,307 A | 2/1996 | Kuslich et al. | |
| 5,490,750 A | 2/1996 | Gundy | |
| 5,496,321 A | 3/1996 | Puno et al. | |
| 5,499,892 A | 3/1996 | Reed | |
| 5,505,731 A | 4/1996 | Tornier | |
| 5,507,745 A | 4/1996 | Logroscino et al. | |
| 5,540,688 A | 7/1996 | Navas | |
| 5,545,165 A | 8/1996 | Biedermann et al. | |
| 5,549,607 A | 8/1996 | Olson et al. | |
| 5,549,608 A * | 8/1996 | Errico et al. | 606/264 |
| 5,554,157 A | 9/1996 | Errico et al. | |
| 5,562,660 A | 10/1996 | Grob | |
| 5,562,663 A | 10/1996 | Wisnewski et al. | |
| 5,569,247 A | 10/1996 | Morrison | |
| 5,569,251 A | 10/1996 | Baker et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,607,304 A | 3/1997 | Bailey et al. | |
| 5,607,425 A | 3/1997 | Rogozinski | |
| 5,607,426 A | 3/1997 | Ralph et al. | |
| 5,607,428 A | 3/1997 | Lin | |
| 5,611,800 A | 3/1997 | Davis et al. | |
| 5,628,740 A | 5/1997 | Mullane | |
| 5,630,817 A | 5/1997 | Rokegem | |
| 5,641,256 A | 6/1997 | Gundy | |
| 5,643,260 A | 7/1997 | Doherty | |
| 5,643,261 A | 7/1997 | Schafer et al. | |
| 5,647,873 A | 7/1997 | Errico et al. | |
| 5,662,652 A | 9/1997 | Schafer et al. | |
| 5,662,653 A | 9/1997 | Songer et al. | |
| 5,669,909 A | 9/1997 | Zdeblick et al. | |
| 5,669,911 A | 9/1997 | Errico et al. | |
| 5,672,175 A | 9/1997 | Martin | |
| 5,672,176 A * | 9/1997 | Biedermann et al. | 606/271 |
| 5,676,703 A | 10/1997 | Gelbard | |
| 5,681,319 A | 10/1997 | Biedermann et al. | |
| 5,683,390 A | 11/1997 | Metz-Stavenhagen et al. | |
| 5,690,630 A | 11/1997 | Errico et al. | |
| 5,697,929 A | 12/1997 | Mellinger | |
| 5,702,393 A * | 12/1997 | Pfaifer | 606/328 |
| 5,711,709 A | 1/1998 | McCoy | |
| 5,713,898 A | 2/1998 | Stucker et al. | |
| 5,716,356 A | 2/1998 | Biedermann et al. | |
| 5,720,751 A | 2/1998 | Jackson | |
| 5,723,013 A | 3/1998 | Jeanson et al. | |
| 5,725,527 A | 3/1998 | Biedermann et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,741,254 A | 4/1998 | Henry et al. | |
| 5,752,957 A | 5/1998 | Ralph et al. | |
| 5,782,830 A | 7/1998 | Farris | |
| 5,782,833 A | 7/1998 | Haider | |
| 5,792,044 A | 8/1998 | Foley et al. | |
| 5,797,911 A | 8/1998 | Sherman et al. | |
| 5,800,435 A | 9/1998 | Errico et al. | |
| 5,800,547 A | 9/1998 | Schafer et al. | |
| 5,810,816 A | 9/1998 | Roussouly et al. | |
| 5,817,094 A | 10/1998 | Errico et al. | |
| 5,863,293 A | 1/1999 | Richelsoph | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,231 A | 5/1999 | Foley et al. | |
| RE36,221 E | 6/1999 | Breard et al. | |
| 5,910,141 A | 6/1999 | Morrison et al. | |
| 5,938,663 A | 8/1999 | Petreto | |
| 5,944,465 A | 8/1999 | Janitzki | |
| 5,951,553 A | 9/1999 | Betz | |
| 5,954,725 A | 9/1999 | Sherman et al. | |
| 5,961,517 A | 10/1999 | Biedermann et al. | |
| 5,964,760 A | 10/1999 | Richelsoph | |
| 5,997,539 A * | 12/1999 | Errico et al. | 606/278 |
| 6,001,098 A | 12/1999 | Metz-Stavenhagen et al. | |
| 6,004,349 A | 12/1999 | Jackson | |
| 6,010,503 A * | 1/2000 | Richelsoph et al. | 606/278 |
| 6,019,759 A | 2/2000 | Rogozinski | |
| 6,022,350 A | 2/2000 | Ganem | |
| 6,053,917 A | 4/2000 | Sherman et al. | |

| | | | |
|---|---|---|---|
| 6,059,786 A | 5/2000 | Jackson | |
| 6,063,090 A * | 5/2000 | Schlapfer | 606/270 |
| 6,074,391 A | 6/2000 | Metz-Stavenhagen et al. | |
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,102,912 A | 8/2000 | Cazin et al. | |
| 6,102,913 A | 8/2000 | Jackson | |
| 6,110,172 A | 8/2000 | Jackson | |
| 6,113,601 A | 9/2000 | Tatar | |
| 6,132,431 A | 10/2000 | Nilsson et al. | |
| 6,132,432 A | 10/2000 | Richelsoph | |
| 6,132,434 A * | 10/2000 | Sherman et al. | 606/78 |
| 6,136,002 A | 10/2000 | Shih et al. | |
| 6,139,549 A | 10/2000 | Keller | |
| 6,143,032 A | 11/2000 | Schafer et al. | |
| 6,146,383 A | 11/2000 | Studer et al. | |
| 6,183,472 B1 | 2/2001 | Lutz | |
| 6,186,718 B1 | 2/2001 | Fogard | |
| 6,187,005 B1 | 2/2001 | Brace et al. | |
| 6,193,720 B1 | 2/2001 | Yuan et al. | |
| 6,214,012 B1 | 4/2001 | Karpman et al. | |
| RE37,161 E | 5/2001 | Michelson et al. | |
| 6,224,596 B1 | 5/2001 | Jackson | |
| 6,224,598 B1 | 5/2001 | Jackson | |
| 6,235,028 B1 | 5/2001 | Brumfield et al. | |
| 6,235,034 B1 | 5/2001 | Bray | |
| 6,241,730 B1 | 6/2001 | Alby | |
| 6,248,105 B1 | 6/2001 | Schlapfer et al. | |
| 6,248,107 B1 | 6/2001 | Foley et al. | |
| 6,251,112 B1 | 6/2001 | Jackson | |
| 6,254,146 B1 | 7/2001 | Church | |
| 6,254,602 B1 | 7/2001 | Justis | |
| 6,267,764 B1 | 7/2001 | Elberg | |
| 6,267,765 B1 | 7/2001 | Taylor et al. | |
| 6,273,888 B1 * | 8/2001 | Justis | 606/272 |
| 6,277,122 B1 | 8/2001 | McGahan et al. | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 * | 9/2001 | Sherman et al. | 606/78 |
| 6,290,700 B1 | 9/2001 | Schmotzer | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,302,888 B1 | 10/2001 | Mellinger et al. | |
| 6,309,391 B1 | 10/2001 | Crandall et al. | |
| 6,315,564 B1 | 11/2001 | Levisman | |
| 6,315,779 B1 | 11/2001 | Morrison et al. | |
| 6,331,179 B1 | 12/2001 | Freid et al. | |
| 6,355,040 B1 * | 3/2002 | Richelsoph et al. | 606/272 |
| RE37,665 E | 4/2002 | Ralph et al. | |
| 6,368,321 B1 | 4/2002 | Jackson | |
| 6,371,957 B1 | 4/2002 | Amrein et al. | |
| 6,402,752 B2 * | 6/2002 | Schaffler-Wachter et al. | 606/266 |
| 6,402,757 B1 | 6/2002 | Moore et al. | |
| 6,440,133 B1 | 8/2002 | Beale et al. | |
| 6,440,137 B1 * | 8/2002 | Horvath et al. | 606/302 |
| 6,443,956 B1 | 9/2002 | Ray | |
| 6,451,021 B1 | 9/2002 | Ralph et al. | |
| 6,471,703 B1 | 10/2002 | Ashman | |
| 6,471,705 B1 * | 10/2002 | Biedermann et al. | 606/271 |
| 6,478,801 B1 | 11/2002 | Ralph et al. | |
| 6,485,491 B1 * | 11/2002 | Farris et al. | 606/250 |
| 6,485,492 B1 | 11/2002 | Halm et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,511,484 B2 | 1/2003 | Torode et al. | |
| 6,520,962 B1 | 2/2003 | Taylor et al. | |
| 6,527,804 B1 | 3/2003 | Gauchet et al. | |
| 6,530,929 B1 | 3/2003 | Jusis et al. | |
| 6,533,786 B1 | 3/2003 | Needham et al. | |
| 6,539,826 B2 | 4/2003 | Oesterle et al. | |
| 6,540,749 B2 | 4/2003 | Schafer et al. | |
| 6,547,790 B2 | 4/2003 | Harkey, III et al. | |
| 6,551,320 B2 | 4/2003 | Lieberman | |
| 6,551,323 B2 | 4/2003 | Doubler et al. | |
| 6,554,831 B1 | 4/2003 | Rivard et al. | |
| 6,554,832 B2 | 4/2003 | Shluzas | |
| 6,554,834 B1 | 4/2003 | Crozet et al. | |
| 6,558,387 B2 | 5/2003 | Errico et al. | |
| 6,562,038 B1 | 5/2003 | Morrison | |
| 6,562,040 B1 | 5/2003 | Wagner | |
| 6,565,565 B1 | 5/2003 | Yuan et al. | |
| 6,565,567 B1 * | 5/2003 | Haider | 606/266 |
| 6,572,618 B1 | 6/2003 | Morrison | |
| 6,582,436 B2 | 6/2003 | Schlapfer et al. | |
| 6,582,466 B1 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,599,294 B2 | 7/2003 | Fuss et al. | |
| 6,610,063 B2 | 8/2003 | Kumar et al. | |
| 6,613,050 B1 * | 9/2003 | Wagner et al. | 606/250 |
| 6,616,667 B1 | 9/2003 | Steiger et al. | |
| 6,616,669 B2 | 9/2003 | Ogilvie | |
| 6,623,485 B2 | 9/2003 | Doubler et al. | |
| 6,626,347 B2 | 9/2003 | Ng | |
| 6,626,907 B2 | 9/2003 | Campbell et al. | |
| 6,626,908 B2 * | 9/2003 | Cooper et al. | 606/266 |
| 6,635,059 B2 | 10/2003 | Randall et al. | |
| 6,635,060 B2 | 10/2003 | Hanson et al. | |
| 6,648,885 B1 | 11/2003 | Friesem | |
| 6,648,887 B2 | 11/2003 | Ashman | |
| 6,648,888 B1 | 11/2003 | Shluzas | |
| 6,652,526 B1 * | 11/2003 | Arafiles | 606/308 |
| 6,652,765 B1 | 11/2003 | Beaty | |
| 6,656,179 B1 | 12/2003 | Schaefer et al. | |
| 6,656,181 B2 | 12/2003 | Dixon et al. | |
| 6,660,004 B2 * | 12/2003 | Barker et al. | 606/328 |
| 6,660,005 B2 * | 12/2003 | Toyama et al. | 606/308 |
| 6,660,006 B2 | 12/2003 | Markworth et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Benlloch et al. | |
| 6,679,833 B2 | 1/2004 | Smith et al. | |
| 6,682,529 B2 | 1/2004 | Stahurski | |
| 6,682,530 B2 | 1/2004 | Dixon et al. | |
| 6,689,133 B2 | 2/2004 | Morrison et al. | |
| 6,689,134 B2 | 2/2004 | Ralph et al. | |
| 6,695,843 B2 | 2/2004 | Biedermann et al. | |
| 6,695,851 B2 | 2/2004 | Zdeblick et al. | |
| 6,699,249 B2 | 3/2004 | Schlapfer et al. | |
| 6,706,045 B2 | 3/2004 | Lin et al. | |
| 6,712,818 B1 | 3/2004 | Michelson | |
| 6,716,213 B2 | 4/2004 | Shitoto | |
| 6,716,214 B1 | 4/2004 | Jackson | |
| 6,716,247 B2 | 4/2004 | Michelson | |
| 6,723,100 B2 * | 4/2004 | Biedermann et al. | 606/308 |
| 6,730,093 B2 | 5/2004 | Saint Martin | |
| 6,730,127 B2 | 5/2004 | Michelson | |
| 6,733,502 B2 | 5/2004 | Altarac et al. | |
| 6,736,816 B2 | 5/2004 | Ritland | |
| 6,736,820 B2 | 5/2004 | Biedermann et al. | |
| 6,740,086 B2 * | 5/2004 | Richelsoph | 606/60 |
| 6,743,231 B1 | 6/2004 | Gray et al. | |
| 6,746,449 B2 | 6/2004 | Jones et al. | |
| 6,746,454 B2 | 6/2004 | Winterbottom et al. | |
| 6,755,829 B1 * | 6/2004 | Bono et al. | 606/308 |
| 6,755,835 B2 | 6/2004 | Schultheiss et al. | |
| 6,755,836 B2 | 6/2004 | Lewis | |
| 6,761,723 B2 | 7/2004 | Buttermann et al. | |
| 6,767,351 B2 | 7/2004 | Orbay et al. | |
| 6,770,075 B2 | 8/2004 | Howland | |
| 6,778,861 B1 | 8/2004 | Liebrecht et al. | |
| 6,780,186 B2 | 8/2004 | Errico et al. | |
| 6,783,527 B2 | 8/2004 | Drewry et al. | |
| 6,783,528 B2 * | 8/2004 | Vincent-Prestigiacomo | 606/246 |
| 6,790,208 B2 | 9/2004 | Oribe et al. | |
| 6,790,209 B2 | 9/2004 | Beale et al. | |
| 6,802,844 B2 | 10/2004 | Ferree | |
| 6,827,719 B2 | 12/2004 | Ralph et al. | |
| 6,830,571 B2 | 12/2004 | Lenke et al. | |

| | | |
|---|---|---|
| 6,835,196 B2 * | 12/2004 | Biedermann et al. .......... 606/308 |
| 6,837,889 B2 * | 1/2005 | Shluzas .......................... 606/270 |
| 6,840,940 B2 | 1/2005 | Ralph et al. |
| 6,843,791 B2 * | 1/2005 | Serhan ........................... 606/272 |
| 6,857,343 B1 | 2/2005 | Easterbrooks et al. |
| 6,858,031 B2 | 2/2005 | Morrison et al. |
| 6,866,664 B2 * | 3/2005 | Schär et al. .................... 606/252 |
| 6,869,432 B2 | 3/2005 | Schlapfer et al. |
| 6,869,433 B2 * | 3/2005 | Glascott ......................... 606/308 |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 * | 3/2006 | Biedermann et al. .......... 606/308 |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E * | 5/2006 | Ralph et al. .................... 606/278 |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 * | 6/2006 | Shluzas ........................ 606/86 A |
| 7,081,116 B1 * | 7/2006 | Carly ............................. 606/264 |
| 7,083,621 B2 | 8/2006 | Shaolian et al. |
| 7,087,057 B2 * | 8/2006 | Konieczynski et al. ....... 606/278 |
| 7,090,674 B2 * | 8/2006 | Doubler et al. ................ 606/277 |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 * | 12/2006 | Shluzas .......................... 606/266 |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 * | 5/2007 | Biedermann ................... 606/308 |
| 7,211,087 B2 | 5/2007 | Young |
| 7,214,227 B2 | 5/2007 | Colleran et al. |
| 7,223,268 B2 * | 5/2007 | Biedermann ................... 606/308 |
| 7,229,441 B2 | 6/2007 | Trieu et al. |
| 7,264,621 B2 * | 9/2007 | Coates et al. .................. 606/250 |
| 7,270,665 B2 | 9/2007 | Morrison et al. |
| 7,276,069 B2 * | 10/2007 | Biedermann et al. .......... 606/250 |
| 7,282,064 B2 | 10/2007 | Chin |
| 7,291,151 B2 | 11/2007 | Alvarez |
| 7,291,153 B2 * | 11/2007 | Glascott ......................... 606/308 |
| 7,294,128 B2 | 11/2007 | Alleyne et al. |
| 7,294,129 B2 | 11/2007 | Hawkins et al. |
| 7,303,563 B2 * | 12/2007 | Poyner et al. .................. 606/279 |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,320,555 B2 * | 1/2008 | Chang et al. ................... 403/122 |
| 7,322,979 B2 | 1/2008 | Crandall et al. |
| 7,322,982 B2 * | 1/2008 | Vincent-Prestigiacomo 606/246 |
| 7,335,201 B2 | 2/2008 | Doubler et al. |
| 7,335,202 B2 * | 2/2008 | Matthis et al. ................. 606/266 |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,445,627 B2 * | 11/2008 | Hawkes et al. ................ 606/269 |
| 7,476,238 B2 | 1/2009 | Panjabi |
| 7,491,208 B2 | 2/2009 | Pond, Jr. et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,575 B2 * | 9/2009 | Colleran et al. ............ 606/86 A |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,678,112 B2 * | 3/2010 | Rezach ............................ 606/60 |
| 7,678,139 B2 * | 3/2010 | Garamszegi et al. .......... 606/328 |
| 7,682,375 B2 | 3/2010 | Ritland |
| 7,682,377 B2 * | 3/2010 | Konieczynski et al. ....... 606/269 |
| 7,695,496 B2 | 4/2010 | Labrom et al. |
| 7,695,498 B2 | 4/2010 | Ritland |
| 7,695,514 B2 | 4/2010 | Kwak |
| 7,758,618 B2 * | 7/2010 | Walder et al. .................. 606/246 |
| 7,763,048 B2 | 7/2010 | Fortin et al. |
| 7,763,052 B2 | 7/2010 | Jahng |
| 7,766,915 B2 * | 8/2010 | Jackson ........................ 606/86 A |
| 7,766,941 B2 | 8/2010 | Paul |
| 7,766,942 B2 | 8/2010 | Patterson et al. |
| 7,766,943 B1 | 8/2010 | Fallin et al. |
| 7,776,067 B2 * | 8/2010 | Jackson .......................... 606/246 |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,351 B2 | 8/2010 | Gordon et al. |
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,819,899 B2 * | 10/2010 | Lancial .......................... 606/246 |
| 7,875,065 B2 * | 1/2011 | Jackson .......................... 606/305 |
| 7,879,075 B2 * | 2/2011 | Shluzas .......................... 606/267 |
| 7,892,259 B2 * | 2/2011 | Biedermann et al. .......... 606/264 |
| 7,896,902 B2 * | 3/2011 | Jeon et al. ...................... 606/246 |
| 7,901,437 B2 * | 3/2011 | Jackson .......................... 606/278 |
| 7,951,172 B2 * | 5/2011 | Chao et al. ..................... 606/265 |
| 7,955,359 B2 * | 6/2011 | Matthis et al. ................. 606/270 |
| 7,967,850 B2 * | 6/2011 | Jackson .......................... 606/301 |
| 2001/0001119 A1 * | 5/2001 | Lombardo ........................ 606/73 |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 * | 3/2002 | Walder et al. .................... 606/61 |

| Publication No. | Date | Name | Class |
|---|---|---|---|
| 2002/0045898 A1 | 4/2002 | Freid et al. | |
| 2002/0058942 A1* | 5/2002 | Biedermann et al. | 606/73 |
| 2002/0068975 A1 | 6/2002 | Teitelbaum et al. | |
| 2002/0072751 A1 | 6/2002 | Jackson | |
| 2002/0077701 A1 | 6/2002 | Kuslich | |
| 2002/0082602 A1* | 6/2002 | Biedermann et al. | 606/61 |
| 2002/0095153 A1 | 7/2002 | Jones et al. | |
| 2002/0111626 A1 | 8/2002 | Ralph et al. | |
| 2002/0133159 A1 | 9/2002 | Jackson | |
| 2002/0143341 A1* | 10/2002 | Biedermann et al. | 606/73 |
| 2002/0173789 A1 | 11/2002 | Howland | |
| 2002/0193795 A1 | 12/2002 | Gertzbein et al. | |
| 2003/0023240 A1 | 1/2003 | Amrein et al. | |
| 2003/0023243 A1* | 1/2003 | Biedermann et al. | 606/73 |
| 2003/0028192 A1* | 2/2003 | Schar et al. | 606/61 |
| 2003/0073996 A1 | 4/2003 | Doubler et al. | |
| 2003/0083657 A1 | 5/2003 | Drewry et al. | |
| 2003/0093078 A1 | 5/2003 | Ritland | |
| 2003/0100896 A1* | 5/2003 | Biedermann et al. | 606/61 |
| 2003/0105460 A1 | 6/2003 | Crandall et al. | |
| 2003/0109880 A1 | 6/2003 | Shirado et al. | |
| 2003/0114852 A1 | 6/2003 | Biedermann et al. | |
| 2003/0125741 A1* | 7/2003 | Biedermann et al. | 606/61 |
| 2003/0149432 A1 | 8/2003 | Frigg et al. | |
| 2003/0153911 A1 | 8/2003 | Shluzas | |
| 2003/0163133 A1 | 8/2003 | Altarac et al. | |
| 2003/0171749 A1 | 9/2003 | Le Couedic et al. | |
| 2003/0176862 A1 | 9/2003 | Taylor et al. | |
| 2003/0191470 A1 | 10/2003 | Ritland | |
| 2003/0199873 A1* | 10/2003 | Richelsoph | 606/61 |
| 2003/0208203 A1 | 11/2003 | Lim et al. | |
| 2003/0208204 A1 | 11/2003 | Bailey et al. | |
| 2003/0212398 A1 | 11/2003 | Jackson | |
| 2003/0216735 A1 | 11/2003 | Altarac et al. | |
| 2003/0220642 A1 | 11/2003 | Freudiger | |
| 2003/0220643 A1 | 11/2003 | Ferree | |
| 2003/0225408 A1 | 12/2003 | Nichols et al. | |
| 2004/0002708 A1 | 1/2004 | Ritland | |
| 2004/0006342 A1 | 1/2004 | Altarac et al. | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0078082 A1 | 4/2004 | Lange | |
| 2004/0087949 A1 | 5/2004 | Bono et al. | |
| 2004/0087952 A1 | 5/2004 | Borgstrom et al. | |
| 2004/0092934 A1 | 5/2004 | Howland | |
| 2004/0097933 A1* | 5/2004 | Lourdel et al. | 606/61 |
| 2004/0116929 A1* | 6/2004 | Barker et al. | 606/61 |
| 2004/0133207 A1 | 7/2004 | Abdou | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0147929 A1 | 7/2004 | Biedermann et al. | |
| 2004/0158247 A1* | 8/2004 | Sitiso et al. | 606/61 |
| 2004/0162560 A1 | 8/2004 | Raynor et al. | |
| 2004/0172022 A1 | 9/2004 | Landry et al. | |
| 2004/0172025 A1 | 9/2004 | Drewry et al. | |
| 2004/0176766 A1* | 9/2004 | Shluzas | 606/65 |
| 2004/0186473 A1* | 9/2004 | Cournoyer et al. | 606/61 |
| 2004/0210216 A1 | 10/2004 | Farris et al. | |
| 2004/0220567 A1 | 11/2004 | Eisermann et al. | |
| 2004/0220671 A1 | 11/2004 | Ralph et al. | |
| 2004/0225289 A1* | 11/2004 | Biedermann et al. | 606/61 |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0236330 A1 | 11/2004 | Purcell et al. | |
| 2004/0249380 A1* | 12/2004 | Glascott | 606/73 |
| 2004/0260283 A1 | 12/2004 | Wu et al. | |
| 2004/0267264 A1 | 12/2004 | Konieczynski et al. | |
| 2005/0027292 A1* | 2/2005 | Bernard et al. | 606/61 |
| 2005/0027296 A1 | 2/2005 | Thramann et al. | |
| 2005/0033298 A1 | 2/2005 | Hawkes et al. | |
| 2005/0038432 A1 | 2/2005 | Shaolian et al. | |
| 2005/0049708 A1 | 3/2005 | Atkinson et al. | |
| 2005/0055026 A1 | 3/2005 | Biedermann et al. | |
| 2005/0065514 A1 | 3/2005 | Studer | |
| 2005/0065515 A1 | 3/2005 | Jahng | |
| 2005/0065516 A1 | 3/2005 | Jahng | |
| 2005/0065517 A1 | 3/2005 | Chin | |
| 2005/0070899 A1 | 3/2005 | Doubler et al. | |
| 2005/0080415 A1 | 4/2005 | Keyer et al. | |
| 2005/0080419 A1* | 4/2005 | Donath | 606/61 |
| 2005/0085812 A1* | 4/2005 | Sherman et al. | 606/61 |
| 2005/0085813 A1 | 4/2005 | Splitler et al. | |
| 2005/0085815 A1 | 4/2005 | Harms et al. | |
| 2005/0085816 A1 | 4/2005 | Michelson | |
| 2005/0096652 A1 | 5/2005 | Burton | |
| 2005/0096654 A1 | 5/2005 | Lin | |
| 2005/0096659 A1* | 5/2005 | Freudiger | 606/73 |
| 2005/0107788 A1 | 5/2005 | Beaurain et al. | |
| 2005/0113927 A1 | 5/2005 | Malek | |
| 2005/0124991 A1 | 6/2005 | Jahng | |
| 2005/0131404 A1 | 6/2005 | Mazda et al. | |
| 2005/0131407 A1 | 6/2005 | Sicvol et al. | |
| 2005/0131413 A1 | 6/2005 | O'Driscoll et al. | |
| 2005/0137597 A1 | 6/2005 | Butler et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0149023 A1 | 7/2005 | Ritland | |
| 2005/0154389 A1 | 7/2005 | Selover et al. | |
| 2005/0154390 A1 | 7/2005 | Biedermann et al. | |
| 2005/0154391 A1* | 7/2005 | Doherty et al. | 606/61 |
| 2005/0159750 A1 | 7/2005 | Doherty | |
| 2005/0165396 A1 | 7/2005 | Fortin et al. | |
| 2005/0165400 A1 | 7/2005 | Fernandez | |
| 2005/0171540 A1 | 8/2005 | Lim et al. | |
| 2005/0171543 A1 | 8/2005 | Timm et al. | |
| 2005/0177156 A1* | 8/2005 | Timm et al. | 606/61 |
| 2005/0177157 A1 | 8/2005 | Jahng | |
| 2005/0182401 A1 | 8/2005 | Timm et al. | |
| 2005/0187548 A1 | 8/2005 | Butler et al. | |
| 2005/0187555 A1 | 8/2005 | Biedermann et al. | |
| 2005/0192571 A1 | 9/2005 | Abdelgany | |
| 2005/0192580 A1* | 9/2005 | Dalton | 606/73 |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203516 A1* | 9/2005 | Biedermann et al. | 606/61 |
| 2005/0203517 A1 | 9/2005 | Jahng et al. | |
| 2005/0203518 A1* | 9/2005 | Biedermann et al. | 606/61 |
| 2005/0203519 A1 | 9/2005 | Harms et al. | |
| 2005/0216001 A1 | 9/2005 | David | |
| 2005/0216003 A1* | 9/2005 | Biedermann et al. | 606/61 |
| 2005/0228501 A1 | 10/2005 | Miller et al. | |
| 2005/0234450 A1 | 10/2005 | Barker | |
| 2005/0234451 A1 | 10/2005 | Markworth | |
| 2005/0234452 A1 | 10/2005 | Malandain | |
| 2005/0234453 A1 | 10/2005 | Shaolian et al. | |
| 2005/0234454 A1 | 10/2005 | Chin | |
| 2005/0234456 A1 | 10/2005 | Malandain | |
| 2005/0240181 A1 | 10/2005 | Boomer et al. | |
| 2005/0240183 A1 | 10/2005 | Vaughan | |
| 2005/0245930 A1 | 11/2005 | Timm et al. | |
| 2005/0251137 A1 | 11/2005 | Ball | |
| 2005/0251139 A1 | 11/2005 | Roh | |
| 2005/0251140 A1 | 11/2005 | Shaolian et al. | |
| 2005/0251141 A1 | 11/2005 | Frigg et al. | |
| 2005/0260058 A1 | 11/2005 | Cassagne, III | |
| 2005/0261685 A1 | 11/2005 | Fortin et al. | |
| 2005/0261687 A1 | 11/2005 | Garamszegi et al. | |
| 2005/0267470 A1 | 12/2005 | McBride | |
| 2005/0267471 A1 | 12/2005 | Biedermann et al. | |
| 2005/0267474 A1 | 12/2005 | Dalton | |
| 2005/0267477 A1 | 12/2005 | Jackson | |
| 2005/0273099 A1* | 12/2005 | Baccelli et al. | 606/61 |
| 2005/0273101 A1 | 12/2005 | Schumacher | |
| 2005/0277919 A1* | 12/2005 | Slivka et al. | 606/61 |
| 2005/0277922 A1 | 12/2005 | Trieu et al. | |
| 2005/0277923 A1* | 12/2005 | Sweeney | 606/61 |
| 2005/0277925 A1 | 12/2005 | Mujwid | |
| 2005/0277927 A1* | 12/2005 | Guenther et al. | 606/61 |
| 2005/0277928 A1* | 12/2005 | Boschert | 606/61 |
| 2005/0277931 A1 | 12/2005 | Sweeney et al. | |
| 2005/0277934 A1 | 12/2005 | Vardiman | |
| 2005/0283152 A1 | 12/2005 | Lindemann et al. | |
| 2005/0283157 A1* | 12/2005 | Coates et al. | 606/73 |

| Publication No. | Date | Name |
|---|---|---|
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1* | 2/2006 | Khalili ............ 606/61 |
| 2006/0025768 A1* | 2/2006 | Iott et al. ............ 606/61 |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084981 A1* | 4/2006 | Shluzas ............ 606/61 |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1* | 4/2006 | Felix ............ 606/61 |
| 2006/0095037 A1* | 5/2006 | Jones et al. ............ 606/61 |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1* | 6/2006 | Biedermann et al. ............ 606/61 |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1* | 7/2006 | Richelsoph et al. ............ 606/61 |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Faliln |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200128 A1 | 9/2006 | Mueller |
| 2006/0200130 A1 | 9/2006 | Hawkins |
| 2006/0200131 A1* | 9/2006 | Chao et al. ............ 606/61 |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1* | 9/2006 | Hoy et al. ............ 606/72 |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1* | 10/2006 | Bono et al. ............ 606/61 |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1* | 12/2006 | Shluzas ............ 606/61 |
| 2006/0276792 A1* | 12/2006 | Ensign et al. ............ 606/61 |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |

| Pub. No. | Date | Name |
|---|---|---|
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0043355 A1* | 2/2007 | Bette et al. ............. 606/61 |
| 2007/0043356 A1 | 2/2007 | Timm |
| 2007/0043357 A1 | 2/2007 | Kirschman |
| 2007/0043358 A1* | 2/2007 | Molz et al. ............. 606/61 |
| 2007/0043359 A1 | 2/2007 | Altarac et al. |
| 2007/0043364 A1 | 2/2007 | Cawley et al. |
| 2007/0049931 A1* | 3/2007 | Justis et al. ............ 606/61 |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1* | 3/2007 | Matthis et al. ............ 606/61 |
| 2007/0055241 A1* | 3/2007 | Matthis et al. ............ 606/61 |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1* | 3/2007 | Cordaro et al. ........... 606/61 |
| 2007/0073293 A1 | 3/2007 | Martz |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1* | 4/2007 | Baccelli .................. 606/61 |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1* | 4/2007 | Biedermann et al. ......... 606/61 |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1* | 4/2007 | Warnick ................ 606/61 |
| 2007/0093828 A1 | 4/2007 | Abdou |
| 2007/0093831 A1* | 4/2007 | Abdelgany et al. ........... 606/61 |
| 2007/0093833 A1 | 4/2007 | Kuiper et al. |
| 2007/0100341 A1* | 5/2007 | Reglos et al. ............. 606/61 |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123860 A1* | 5/2007 | Francis et al. ............ 606/61 |
| 2007/0123862 A1 | 5/2007 | Warnick |
| 2007/0123864 A1 | 5/2007 | Walder et al. |
| 2007/0123865 A1* | 5/2007 | Schlapfer et al. ............ 606/61 |
| 2007/0123866 A1 | 5/2007 | Gerbec et al. |
| 2007/0123867 A1* | 5/2007 | Kirschman ............... 606/61 |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1* | 7/2007 | Biedermann et al. ......... 606/61 |
| 2007/0161997 A1 | 7/2007 | Thramann et al. |
| 2007/0161999 A1 | 7/2007 | Biedermann et al. ......... 606/61 |
| 2007/0162008 A1* | 7/2007 | Cline et al. .............. 606/61 |
| 2007/0167948 A1 | 7/2007 | Abdou |
| 2007/0167949 A1* | 7/2007 | Altarac et al. ............ 606/61 |
| 2007/0173818 A1 | 7/2007 | Hestad et al. |
| 2007/0173819 A1* | 7/2007 | Sandlin ................. 606/61 |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1* | 9/2007 | Young ................. 606/61 |
| 2007/0213720 A1 | 9/2007 | Gordon et al. |
| 2007/0225707 A1* | 9/2007 | Wisnewski et al. ............ 606/61 |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1* | 10/2007 | Na et al. ............... 606/61 |
| 2007/0233085 A1 | 10/2007 | Biedermann et al. |
| 2007/0233086 A1 | 10/2007 | Harms et al. |
| 2007/0233087 A1* | 10/2007 | Schlapfer ............... 606/61 |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0260246 A1* | 11/2007 | Biedermann ............ 606/61 |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1* | 1/2008 | Whipple ............... 606/61 |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |

| Publication No. | Date | Inventor(s) | Class |
|---|---|---|---|
| 2008/0051780 A1 | 2/2008 | Vaidya et al. | |
| 2008/0051787 A1 | 2/2008 | Remington et al. | |
| 2008/0058811 A1 | 3/2008 | Alleyne et al. | |
| 2008/0058812 A1 | 3/2008 | Zehnder | |
| 2008/0065071 A1 | 3/2008 | Park | |
| 2008/0065073 A1 | 3/2008 | Perriello et al. | |
| 2008/0065075 A1 | 3/2008 | Dant | |
| 2008/0065077 A1 | 3/2008 | Ferree | |
| 2008/0065079 A1 | 3/2008 | Bruneau et al. | |
| 2008/0071273 A1 | 3/2008 | Hawkes et al. | |
| 2008/0071274 A1 | 3/2008 | Enisgn | |
| 2008/0071277 A1* | 3/2008 | Warnick | 606/73 |
| 2008/0077139 A1 | 3/2008 | Landry et al. | |
| 2008/0086131 A1 | 4/2008 | Daly et al. | |
| 2008/0086132 A1 | 4/2008 | Biedermann et al. | |
| 2008/0091214 A1 | 4/2008 | Richelsoph | |
| 2008/0097431 A1 | 4/2008 | Vessa | |
| 2008/0097434 A1 | 4/2008 | Moumene et al. | |
| 2008/0097441 A1 | 4/2008 | Hayes et al. | |
| 2008/0097457 A1 | 4/2008 | Warnick | |
| 2008/0108992 A1 | 5/2008 | Barry et al. | |
| 2008/0119858 A1 | 5/2008 | Potash | |
| 2008/0125777 A1 | 5/2008 | Veldman et al. | |
| 2008/0125787 A1 | 5/2008 | Doubler et al. | |
| 2008/0132952 A1 | 6/2008 | Malandain et al. | |
| 2008/0140075 A1 | 6/2008 | Ensign et al. | |
| 2008/0140076 A1 | 6/2008 | Jackson | |
| 2008/0140133 A1 | 6/2008 | Allard et al. | |
| 2008/0147122 A1 | 6/2008 | Jackson | |
| 2008/0154307 A1 | 6/2008 | Colleran et al. | |
| 2008/0154308 A1* | 6/2008 | Sherman et al. | 606/265 |
| 2008/0161854 A1 | 7/2008 | Bae et al. | |
| 2008/0161859 A1 | 7/2008 | Nilsson | |
| 2008/0161863 A1* | 7/2008 | Arnold et al. | 606/319 |
| 2008/0167687 A1 | 7/2008 | Colleran et al. | |
| 2008/0177316 A1 | 7/2008 | Bergeronk et al. | |
| 2008/0177317 A1 | 7/2008 | Jackson | |
| 2008/0177319 A1 | 7/2008 | Schwab | |
| 2008/0177321 A1 | 7/2008 | Drewry et al. | |
| 2008/0177322 A1 | 7/2008 | Davis et al. | |
| 2008/0177327 A1 | 7/2008 | Malandain et al. | |
| 2008/0183212 A1 | 7/2008 | Veldman et al. | |
| 2008/0183213 A1 | 7/2008 | Veldman et al. | |
| 2008/0183214 A1* | 7/2008 | Copp et al. | 606/265 |
| 2008/0183215 A1 | 7/2008 | Altarac et al. | |
| 2008/0183216 A1* | 7/2008 | Jackson | 606/278 |
| 2008/0183223 A1 | 7/2008 | Jeon et al. | |
| 2008/0195100 A1 | 8/2008 | Capote et al. | |
| 2008/0195153 A1 | 8/2008 | Thompson | |
| 2008/0195156 A1* | 8/2008 | Ainsworth et al. | 606/279 |
| 2008/0215095 A1 | 9/2008 | Biedermann et al. | |
| 2008/0221620 A1 | 9/2008 | Krause | |
| 2008/0221692 A1 | 9/2008 | Zucherman et al. | |
| 2008/0228227 A1 | 9/2008 | Brown et al. | |
| 2008/0228229 A1 | 9/2008 | Walder et al. | |
| 2008/0234691 A1 | 9/2008 | Schwab | |
| 2008/0234734 A1* | 9/2008 | Walder et al. | 606/246 |
| 2008/0234736 A1 | 9/2008 | Trieu et al. | |
| 2008/0234737 A1 | 9/2008 | Bosehert | |
| 2008/0234739 A1 | 9/2008 | Hudgins et al. | |
| 2008/0234744 A1 | 9/2008 | Zylber et al. | |
| 2008/0234746 A1 | 9/2008 | Jahng et al. | |
| 2008/0234757 A1* | 9/2008 | Jacofsky et al. | 606/308 |
| 2008/0243188 A1 | 10/2008 | Walder | |
| 2008/0249570 A1* | 10/2008 | Carson et al. | 606/264 |
| 2008/0255617 A1 | 10/2008 | Cho et al. | |
| 2008/0262546 A1 | 10/2008 | Calvosa et al. | |
| 2008/0262548 A1 | 10/2008 | Lange et al. | |
| 2008/0262552 A1 | 10/2008 | Kim | |
| 2008/0262554 A1 | 10/2008 | Hayes et al. | |
| 2008/0269804 A1 | 10/2008 | Holt | |
| 2008/0275504 A1 | 11/2008 | Bonin et al. | |
| 2008/0287994 A1 | 11/2008 | Perez-Cruet et al. | |
| 2008/0300630 A1 | 12/2008 | Bohnema et al. | |
| 2008/0300633 A1 | 12/2008 | Jackson | |
| 2008/0306528 A1 | 12/2008 | Winslow et al. | |
| 2008/0306533 A1 | 12/2008 | Winslow et al. | |
| 2008/0306536 A1 | 12/2008 | Frig et al. | |
| 2008/0306539 A1 | 12/2008 | Cain et al. | |
| 2008/0306540 A1 | 12/2008 | Mitchell et al. | |
| 2008/0306543 A1 | 12/2008 | Cain et al. | |
| 2008/0306545 A1 | 12/2008 | Winslow | |
| 2008/0312694 A1 | 12/2008 | Peterman et al. | |
| 2009/0005817 A1* | 1/2009 | Friedrich et al. | 606/246 |
| 2009/0012567 A1* | 1/2009 | Biedermann et al. | 606/264 |
| 2009/0018583 A1 | 1/2009 | Song et al. | |
| 2009/0024165 A1 | 1/2009 | Ferree | |
| 2009/0024169 A1 | 1/2009 | Triplett et al. | |
| 2009/0030464 A1 | 1/2009 | Hestad et al. | |
| 2009/0030465 A1 | 1/2009 | Altarac et al. | |
| 2009/0048631 A1 | 2/2009 | Bhatnagar et al. | |
| 2009/0054932 A1 | 2/2009 | Butler et al. | |
| 2009/0069849 A1* | 3/2009 | Oh et al. | 606/246 |
| 2009/0082815 A1 | 3/2009 | Zylber et al. | |
| 2009/0088782 A1 | 4/2009 | Moumene et al. | |
| 2009/0088799 A1 | 4/2009 | Yeh | |
| 2009/0088803 A1 | 4/2009 | Justis et al. | |
| 2009/0093820 A1 | 4/2009 | Trieu et al. | |
| 2009/0093843 A1 | 4/2009 | Lemoine et al. | |
| 2009/0093845 A1 | 4/2009 | Hestad et al. | |
| 2009/0093846 A1 | 4/2009 | Hestad et al. | |
| 2009/0099606 A1 | 4/2009 | Hestad et al. | |
| 2009/0099607 A1 | 4/2009 | Fallin et al. | |
| 2009/0099608 A1 | 4/2009 | Szczesny | |
| 2009/0105760 A1 | 4/2009 | Frey | |
| 2009/0112265 A1 | 4/2009 | Hudgins et al. | |
| 2009/0112266 A1 | 4/2009 | Weng et al. | |
| 2009/0112267 A1 | 4/2009 | Atkinson et al. | |
| 2009/0118767 A1* | 5/2009 | Hestad et al. | 606/279 |
| 2009/0125063 A1 | 5/2009 | Panjabi | |
| 2009/0131981 A1 | 5/2009 | White | |
| 2009/0138052 A1 | 5/2009 | Biedermann et al. | |
| 2009/0149885 A1 | 6/2009 | Durward et al. | |
| 2009/0163953 A1 | 6/2009 | Biedermann et al. | |
| 2009/0163954 A1 | 6/2009 | Kwak | |
| 2009/0163955 A1 | 6/2009 | Moumene et al. | |
| 2009/0171395 A1 | 7/2009 | Jeon et al. | |
| 2009/0177232 A1 | 7/2009 | Kiester | |
| 2009/0192548 A1 | 7/2009 | Jeon et al. | |
| 2009/0198281 A1 | 8/2009 | Rice et al. | |
| 2009/0228045 A1 | 9/2009 | Hayes et al. | |
| 2009/0240286 A1 | 9/2009 | Friedrich et al. | |
| 2009/0240287 A1 | 9/2009 | Cunliffe et al. | |
| 2009/0248075 A1 | 10/2009 | Ogilvie et al. | |
| 2009/0248077 A1 | 10/2009 | Johns | |
| 2009/0248081 A1 | 10/2009 | LeHuec et al. | |
| 2009/0248083 A1 | 10/2009 | Patterson et al. | |
| 2009/0248088 A1 | 10/2009 | Biedermann | |
| 2009/0254123 A1 | 10/2009 | Pafford et al. | |
| 2009/0259257 A1 | 10/2009 | Prevost | |
| 2009/0259258 A1 | 10/2009 | Perez-Cruet et al. | |
| 2009/0270917 A1 | 10/2009 | Boehm | |
| 2009/0270920 A1 | 10/2009 | Douget et al. | |
| 2009/0270921 A1 | 10/2009 | Krause | |
| 2009/0270922 A1 | 10/2009 | Biedermann et al. | |
| 2009/0275981 A1 | 11/2009 | Abdelgany et al. | |
| 2009/0275983 A1 | 11/2009 | Veldman et al. | |
| 2009/0275986 A1 | 11/2009 | Prevost et al. | |
| 2009/0281572 A1 | 11/2009 | White | |
| 2009/0281573 A1 | 11/2009 | Biedermann et al. | |
| 2009/0287250 A1 | 11/2009 | Molz, IV et al. | |
| 2009/0287251 A1 | 11/2009 | Bae et al. | |
| 2009/0287252 A1 | 11/2009 | Marik et al. | |
| 2009/0299411 A1 | 12/2009 | Laskowitz et al. | |
| 2009/0318968 A1 | 12/2009 | Duggal et al. | |
| 2009/0326582 A1 | 12/2009 | Songer et al. | |
| 2009/0326583 A1 | 12/2009 | Moumene et al. | |
| 2010/0010544 A1* | 1/2010 | Fallin et al. | 606/264 |
| 2010/0030271 A1 | 2/2010 | Winslow et al. | |
| 2010/0036420 A1 | 2/2010 | Kalfas et al. | |
| 2010/0036422 A1 | 2/2010 | Flynn et al. | |
| 2010/0036423 A1 | 2/2010 | Hayes et al. | |
| 2010/0036424 A1 | 2/2010 | Fielding et al. | |
| 2010/0036425 A1 | 2/2010 | Barrus et al. | |
| 2010/0042155 A1 | 2/2010 | Biedermann et al. | |
| 2010/0042156 A1 | 2/2010 | Harms et al. | |
| 2010/0049254 A1 | 2/2010 | Biedermann et al. | |
| 2010/0057125 A1 | 3/2010 | Viker | |

| | | | |
|---|---|---|---|
| 2010/0057126 A1 | 3/2010 | Hestad | |
| 2010/0063544 A1 | 3/2010 | Butler | |
| 2010/0063545 A1 | 3/2010 | Richelsoph | |
| 2010/0063547 A1 | 3/2010 | Morin et al. | |
| 2010/0063551 A1 | 3/2010 | Richelsoph | |
| 2010/0069964 A1 | 3/2010 | Lechmann | |
| 2010/0087858 A1 | 4/2010 | Abdou | |
| 2010/0087862 A1 | 4/2010 | Biedermann et al. | |
| 2010/0087863 A1 | 4/2010 | Biedermann et al. | |
| 2010/0087865 A1 | 4/2010 | Biedermann et al. | |
| 2010/0094344 A1* | 4/2010 | Trieu | 606/246 |
| 2010/0094348 A1 | 4/2010 | Biedermann et al. | |
| 2010/0174313 A1* | 7/2010 | Abdelgany et al. | 606/246 |
| 2010/0198261 A1 | 8/2010 | Trieu et al. | |
| 2010/0198269 A1 | 8/2010 | Taylor et al. | |
| 2010/0204736 A1 | 8/2010 | Biedermann et al. | |
| 2010/0211104 A1 | 8/2010 | Moumene et al. | |
| 2010/0222819 A1 | 9/2010 | Timm et al. | |
| 2010/0228292 A1 | 9/2010 | Arnold et al. | |
| 2010/0249843 A1 | 9/2010 | Wegzyn, III | |
| 2010/0249845 A1* | 9/2010 | Meunier et al. | 606/263 |
| 2010/0256682 A1 | 10/2010 | Fallin et al. | |
| 2010/0262187 A1 | 10/2010 | Marik et al. | |
| 2010/0262190 A1 | 10/2010 | Ballard et al. | |
| 2010/0274285 A1 | 10/2010 | Rouleau | |
| 2010/0274287 A1 | 10/2010 | Rouleau et al. | |
| 2010/0274288 A1 | 10/2010 | Prevost et al. | |
| 2011/0004245 A1* | 1/2011 | Wu et al. | 606/246 |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 9202745.8 | 4/1992 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO96/41582 | 12/1996 |
| WO | WO9641582 | 12/1996 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | 2007/124249 | 11/2007 |
| WO | WO2007/124222 | 11/2007 |
| WO | WO2007/130835 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation Advertisement*, Blackstone Medical Inc., no publish date.
*The Moss Miami 6.0mm System Advertisement*, author unknown, no publish date.
Brochure of Sofamor Danek the Spine Specialist, TSRH, Pedicle Screw Spinal System, Publication Date: Jan. 23, 1995.
Brochure of Spinal Concepts, an Abbott Laboratories Company, Pathfinder, Minimally Invasive Pedicle Fixation System, Publication Date: Nov. 2003.
Brochure of Spinal Concepts, InCompass, Thoracolumbar Fixation System, Publication Date: Oct. 2003.
Brochure of Spinal Concepts, Pathfinder, Minimally Invasive Pedicle Fixation System, Publication Date: May 2003.
Brochure of Spinal Concepts, Surgical Technique, InCompass, Thoracolumbar Fixation System, Publication Date: Oct. 2003.
Brochure of SpineLine, Current Concepts, Minimally Invasive Posterior Spinal Decompression and Fusion Procedures, Publication Date: Sep./Oct. 2003.
Date: Sep. 2001, pp. 1-8.
Brochure of Zimmer Spine, Inc., Dynesys® LIS Less Invasive Surgery, The Dynamic Stabilization System, Publication Date: 2005.
VLS System Variable Locking Screw Brochure, Interpore Cross International, 1999.

\* cited by examiner

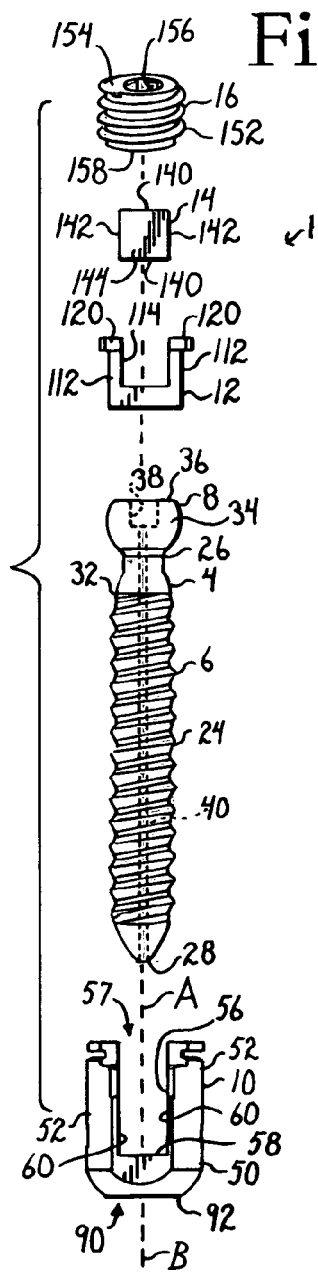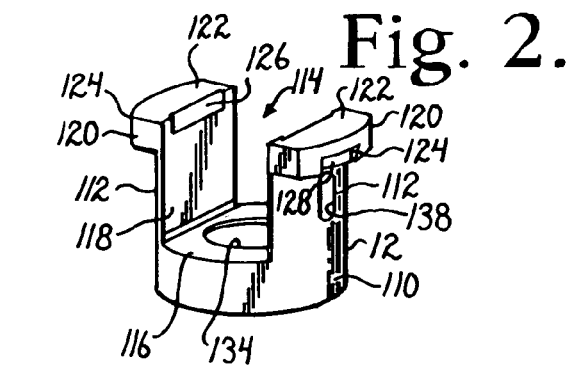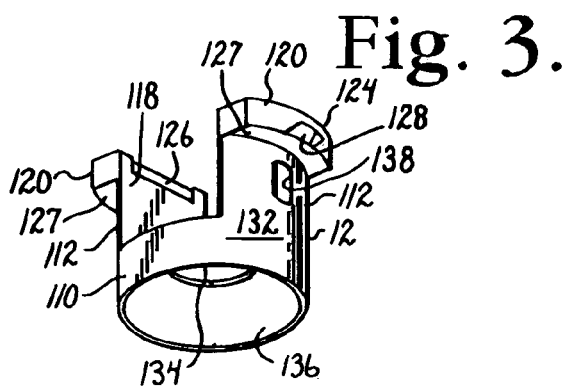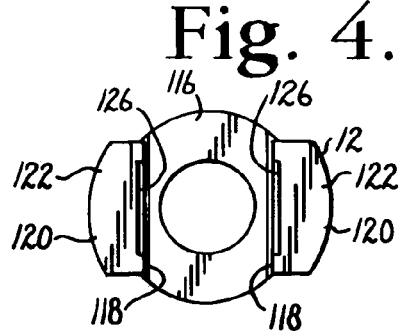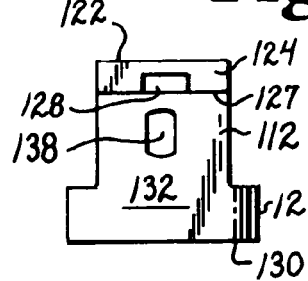

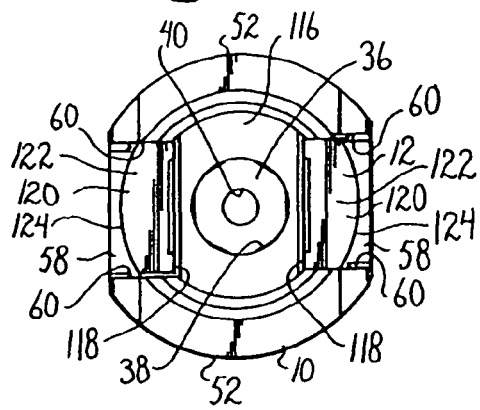
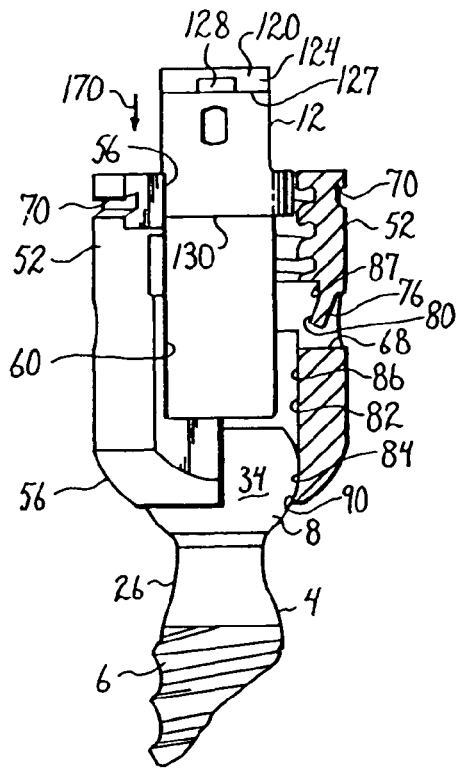
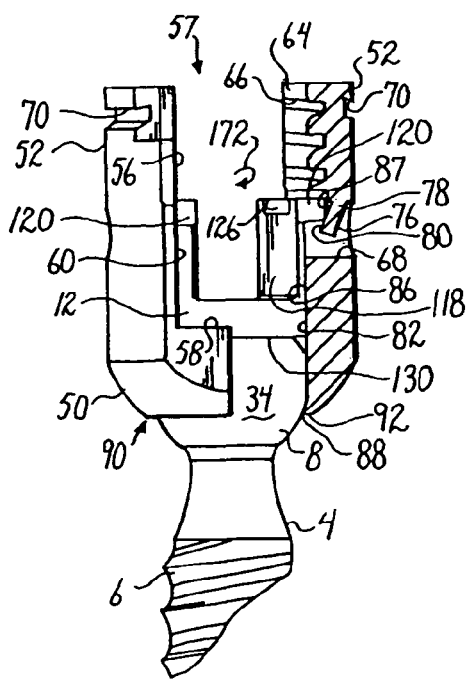

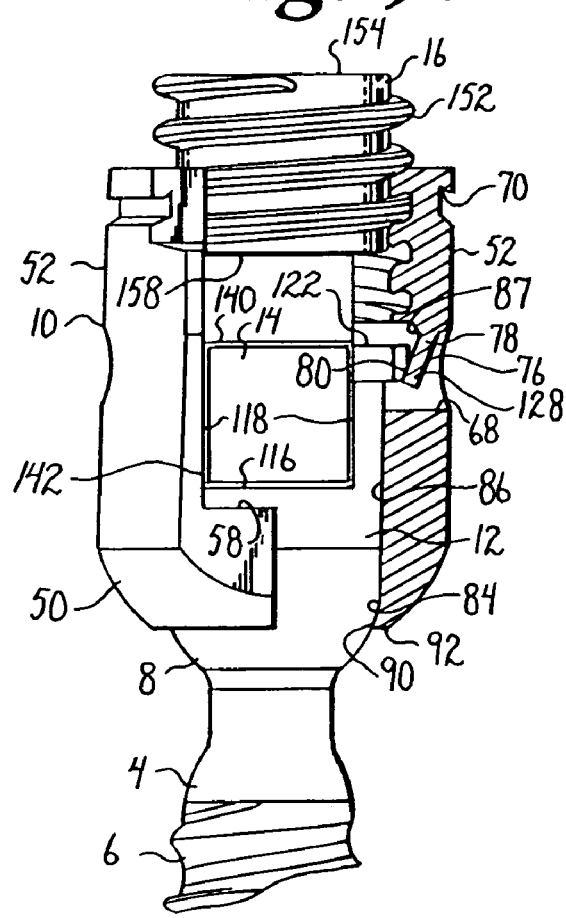
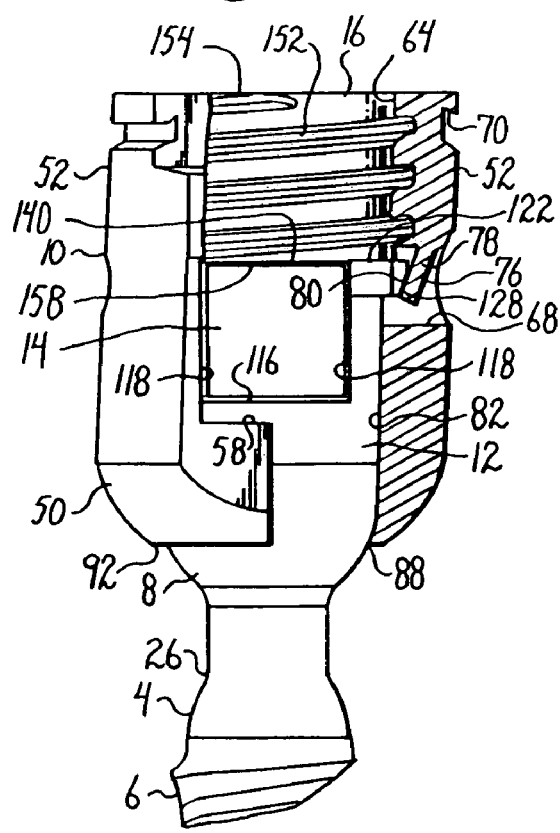

POLYAXIAL BONE ANCHOR ASSEMBLY WITH ONE-PIECE CLOSURE, PRESSURE INSERT AND PLASTIC ELONGATE MEMBER

CROSS-REFERENCE TO RELATED APPLICATIONS

This application claims the benefit of U.S. Provisional Application No. 60/994,083 filed Sep. 17, 2007, incorporated by reference herein. This application is also a continuation-in-part of U.S. patent application Ser. No. 11/894,001 filed Aug. 17, 2007 now U.S. Pat. No. 8,292,926 that claims the benefit of U.S. Provisional Application Nos. 60/851,353 filed Oct. 12, 2006 and 60/905,472 filed Mar. 7, 2007; the disclosures all of which are incorporated by reference herein. This application is also a continuation-in-part of U.S. patent application Ser. No. 11/522,503, filed Sep. 14, 2006 now U.S. Pat. No. 7,766,915 that claims the benefit of U.S. Provisional Application Nos. 60/722,300 filed Sep. 30, 2005; 60/725,445, filed Oct. 11, 2005; 60/728,912, filed Oct. 21, 2005; 60/736, 112 filed Nov. 10, 2005; and 60/832,644, filed Jul. 21, 2006; the disclosures all of which are incorporated by reference herein. This application is also a continuation-in-part of U.S. patent application Ser. No. 12/008,067, filed Jan. 8, 2008 that claims the benefit of U.S. Provisional Application No. 60/897,723, filed Jan. 26, 2007.

BACKGROUND OF THE INVENTION

The present invention is directed to polyaxial bone screws for use in bone surgery, particularly spinal surgery, and elongate connecting members that are at least somewhat plastically deformable. Such screws have a receiver or head that can swivel about a shank of the bone screw, allowing the receiver to be positioned in any of a number of angular configurations relative to the shank.

Many spinal surgery procedures require securing various implants to bone and especially to vertebrae along the spine. For example, elongate or longitudinal connecting members, such as solid rigid rods are often utilized that extend along the spine to provide support to vertebrae that have been damaged or weakened due to injury or disease. Such elongate members must be supported by certain vertebrae and support other vertebrae.

The most common mechanism for providing vertebral support is to implant bone screws into certain bones which then in turn support the elongate member or are supported by the elongate member. Bone screws of this type may have a fixed head or receiver relative to a shank thereof. In the fixed bone screws, the head cannot be moved relative to the shank and the rod or other elongate member must be favorably positioned in order for it to be placed within the head. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod or other elongate connecting member can be inserted into the receiver and eventually the rod and the receiver are locked or fixed in a particular position relative to the shank.

A variety of polyaxial or swivel-head bone screw assemblies are available. One type of bone screw assembly includes an open head or receiver that allows for placement of a rod or other elongate member within the receiver. A closure top or plug is then used to capture the rod in the receiver of the screw. Thus, in such bone screws, the closure top or plug pressing against the rod not only locks the rod in place but also locks the bone screw shank in a desired angular position with respect to the receiver. A draw back to such a system occurs when the rod or other elongate connecting member is made from a material that is more flexible and may be more readily deformed or exhibit creep or viscoelastic behavior. Creep is a term used to describe the tendency of a material to move, flow or to deform permanently to relieve stresses. Material deformation occurs as a result of long term exposure to levels of stress that are below the yield or ultimate strength of the material. Rods and other longitudinal connecting members made from polymers, such as polyetheretherketone (PEEK), have a greater tendency to exhibit creep, than, for example metals or metal alloys. When a rod or other longitudinal connecting member exhibits creep deformation over time, the closure top may no longer tightly engage the connecting member. This in itself is not necessarily problematic. However, such loosening also results in loosening of the frictional engagement between the receiver and the bone screw shank that locks the angular orientation of the shank with respect to the receiver. Body movement and stresses may then result in undesirable pivoting of the shank with respect to the receiver causing mis-alignment, greater stress and further loosening of the various polyaxial bone screw components.

SUMMARY OF THE INVENTION

A polyaxial bone screw assembly of the present invention includes a shank having a generally elongate body with an upper end portion and a lower threaded portion for fixation to a bone. The bone screw assembly further includes a receiver having a top portion and a base. The top portion is open and has a channel. The base includes an inner seating surface partially defining a cavity and has a lower aperture or opening. The channel of the top portion communicates with the cavity, which in turn communicates with an opening to an exterior of the base. The shank upper portion is disposed in the receiver cavity and the shank extends through the receiver base opening. The cooperating shapes of the shank upper portion external surface and the receiver inner surface enable selective angular positioning of the shank body with respect to the receiver. The shank upper surface engages a compression insert that in turn engages a longitudinal connecting member being supported within the receiver. In certain embodiments, the compression insert includes a planar bottom seat and spaced planar sides for closely receiving an elongate connecting member that has planar sides. Such a compression insert can also receive a cylindrical or other shaped connecting member. A single-piece closure structure initially engages the connecting member and, after some plastic deformation of such member, then the closure structure engages the compression insert for securing the assembly in a wide range of angular orientations.

OBJECTS AND ADVANTAGES OF THE INVENTION

Objects of the invention include: providing an implant wherein all of the parts remain together and do not separate; providing a lightweight, low profile polyaxial bone screw that assembles in such a manner that the components cooperate to create an overall structure that prevents unintentional disassembly; providing a polyaxial bone screw that provides substantially independent locking for the bone screw shank and a deformable longitudinal connecting member; providing such an assembly that includes a flexible longitudinal connecting member that may be of non-circular or circular cross-section; providing such an assembly that remains in a locked position even if the flexible longitudinal connecting member undergoes deformation such as creep; providing a polyaxial bone screw with features that provide adequate frictional or gripping surfaces for bone implantation tools and may be readily, securely fastened to each other and to bone; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded front elevational view of a medical implant assembly according to the invention including a polyaxial bone screw having a receiver, a bone screw shank, a lower compression insert and a closure structure cooperating with a longitudinal connecting member in the form of a bar of non-circular cross-section.

FIG. 2 is an enlarged upper perspective view of the compression insert of FIG. 1.

FIG. 3 is an enlarged lower perspective view of the compression insert of FIG. 1.

FIG. 4 is an enlarged top plan view of the compression insert of FIG. 1.

FIG. 5 is an enlarged side elevational view of the compression insert of FIG. 1.

FIG. 6 is an enlarged top plan view of the bone screw shank, receiver and the insert being shown during assembly of the insert into the receiver.

FIG. 7 is an enlarged and partial front elevational view of the bone screw shank, receiver and insert, also showing the insert in a stage of assembly similar to FIG. 6.

FIG. 8 is an enlarged and partial front elevational view of the bone screw shank, receiver, insert and longitudinal connecting member of FIG. 1 shown assembled and with portions broken away to show the detail thereof.

FIG. 9 is an enlarged and partial front elevational view of the bone screw shank, receiver, insert and longitudinal connecting member of FIG. 1 shown assembled and further shown with the closure structure of FIG. 1 in an early stage of assembly with the receiver and with portions broken away to show the detail thereof.

FIG. 10 is an enlarged and partial front elevational view of the bone screw shank, receiver, insert and longitudinal connecting member of FIG. 1 shown assembled with the closure structure of FIG. 1 and with portions broken away to show the detail thereof.

DETAILED DESCRIPTION OF THE INVENTION

Figure 11:
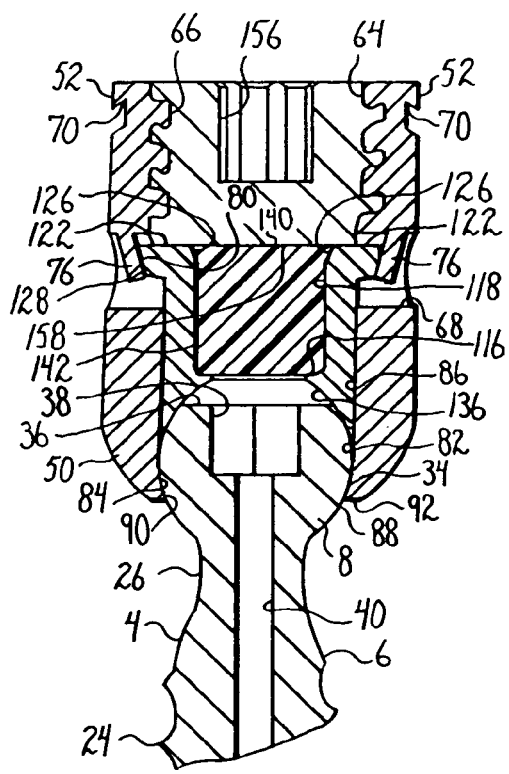
FIG. 11 is an enlarged and partial view similar to FIG. 10 with additional portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-13, the reference number 1 generally represents an embodiment of a medical implant assembly according to the present invention. The assembly 1 includes a polyaxial bone screw 3 having a shank 4 that further includes a threaded body 6 integral with an upper portion 8; a receiver 10; and a lower compression or pressure insert 12. The medical implant assembly 1 further includes a longitudinal connecting member 14 and a closure structure 16. The shank 4, receiver 10, and compression insert 12 are typically factory assembled prior to implantation of the shank body 6 into a vertebra (not shown).

As will be described in greater detail below, the illustrated shank 4 is top loaded into the receiver 10 and thereafter the substantially spherical upper portion 8 slidingly cooperates with an inner substantially spherical inner surface of the receiver 10 such that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. It is noted that although the drawing figures show a top loaded polyaxial mechanism having a spherical sliding connection between the shank upper portion and the receiver inner surface, other kinds of top loaded and bottom loaded embodiments may be utilized according to the invention. For example, bottom loaded bone screws, such as that disclosed in Applicant's U.S. Pat. Pub. No. 2007/0055244 (U.S. patent application Ser. No.

11/522,503 filed Sep. 14, 2006), the disclosure of which is incorporated by reference herein, having a threaded capture connection between a shank upper portion and a retainer structure disposed within the receiver may be utilized for providing a polyaxial connection between the receiver and the shank for use with the present invention. Specifically, U.S. Pat. Pub. No. 2007/0055244 discloses a bone screw shank that includes an upper portion that further includes an outer helical thread mateable with a retaining structure that includes a mating inner helical thread. The retaining structure has a partially spherical surface that is slidingly mateable with a cooperating inner surface of the receiver, allowing for a wide range of pivotal movement between the shank and the receiver. Bottom or top loaded polyaxial bone screws with other types of capture connections may also be used according to the invention, including but not limited to other types of threaded connections, frictional connections utilizing frusto-conical or polyhedral capture structures, or other integral top or downloadable shanks.

The shank 4, best illustrated in FIGS. 1 and 9, is elongate, with the shank body 6 having a helically wound bone implantable thread 24 extending from near a neck 26 located adjacent to the upper portion 8 to a tip 28 of the body 6 and extending radially outwardly therefrom. During use, the body 6 utilizing the thread 24 for gripping and advancement is implanted into the vertebra (not shown) leading with the tip 28 and driven down into the vertebra with an installation or driving tool, so as to be implanted in the vertebra to near the neck 26. The shank 4 has an elongate axis of rotation generally identified by the reference letter A.

The neck 26 extends axially upwardly from the shank body 6. The neck 26 may be of reduced radius as compared to an adjacent top 32 of the threaded body 6. Further extending axially upwardly from the neck 26 is the shank upper portion 8 that provides a connective or capture apparatus disposed at a distance from the threaded body top 32 and thus at a distance from the vertebra when the body 6 is implanted in the vertebra.

The shank upper portion 8 is configured for a polyaxial connection between the shank 4 and the receiver 10 and capturing the shank 4 upper portion 8 in the receiver 10. The upper portion 8 generally includes an outer spherical surface 34; a planar annular upper surface 36 and with an internal drive feature or structure 38 formed in the surface 36. A driving tool (not shown) has a driving projection configured to fit within the tool engagement structure 38 for both driving and rotating the shank body 6 into the vertebra. As best shown in FIG. 11, the spherical surface 34 is also sized and shaped for sliding contact engagement and ultimate positive frictional mating engagement with the compression insert 12, when the bone screw 3 is assembled, and in any alignment of the shank 4 relative to the receiver 10. The illustrated surface 34 also has approximately the same radius as an inner spherical seating surface (84 described in greater detail below) of the receiver 10, allowing for clearance of the shank 4 with respect to the receiver 10 and thus a desired degree and magnitude of articulation of the shank 4 with respect to the receiver 10. In certain embodiments, the surface 34 is smooth. While not required in accordance with the practice of the invention, the surface 34 may be scored or knurled to further increase frictional positive mating engagement between the surface 34 and the compression insert 12.

The shank 4 shown in the drawings is cannulated, having a small central bore 40 extending an entire length of the shank 4 along the axis A. The bore 40 is defined by an inner cylindrical wall of the shank 4 and has a circular opening at the shank tip 28 and an upper opening communicating with the internal drive 38. The bore 40 is coaxial with the threaded body 6 and the upper portion 8. The bore 40 provides a passage through the shank 4 interior for a length of wire (not shown) inserted into the vertebra (not shown) prior to the insertion of the shank body 6, the wire providing a guide for insertion of the shank body 6 into the vertebra (not shown).

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Referring to FIGS. 1 and 6-12, the receiver 10 has a generally squared off U-shaped appearance with a partially cylindrical inner profile and a substantially curved or cylindrical outer profile; however, the outer profile could also be of another configuration, for example, faceted. The receiver has an axis of rotation B that is shown in FIG. 1 as being aligned with and the same as the axis of rotation A of the shank 4, such orientation being desirable during assembly of the receiver 10 with the shank 4 and the insert 12. After such assembly, the bone screw 3 is implanted in a vertebra (not shown). Thereafter, the axis B is typically disposed at an angle with respect to the axis A of the shank 4.

The receiver 10 includes a base 50 integral with a pair of opposed substantially similar or identical upstanding arms 52 forming a squared-off U-shaped cradle and defining a channel 56 between the arms 52 with an upper opening 57 and a lower planar seat 58. The channel 56 is defined in part by planar opposed parallel walls 60 of the receiver arms 52 that run perpendicular to the lower planar seat 58. The walls 60 are spaced to closely receive the bar-shaped connecting member 14 but may also receive a cylindrical rod or oval rod having a diameter or width the same or less than a width of the connecting member 14.

Each of the arms 52 has an interior surface 64 that defines the inner cylindrical profile and includes a partial helically wound guide and advancement structure 66. In the illustrated embodiment, the guide and advancement structure 66 is a partial helically wound interlocking flange form configured to mate under rotation with a similar structure on the closure structure 16, as described more fully below. However, it is foreseen that the guide and advancement structure 66 could alternatively be a square thread, a buttress thread, a reverse angle thread or other thread like or non-thread like helically wound advancement structure for operably guiding under rotation and advancing the closure top downward between the arms 52.

Opposed tool engaging apertures 68 are formed on or through surfaces of the arms 52 that may be used for holding the receiver 10 during assembly with the shank 4 and the retainer structure 12 and also during the implantation of the shank body 6 into a vertebra (not shown). Furthermore, the illustrated embodiment includes upper undercut tool engaging grooves 70 for cooperating with manipulation tools. It is foreseen that tool receiving grooves or apertures may be configured in a variety of shapes and sizes and be disposed at other locations on the receiver arms 52.

A pair of spring tabs 76, each having an upper body portion 78 integral with a respective arm 52, and a lower and inner surface 80 extending below the respective upper body portion 78. The surface 80 is sized and shaped for frictional contact with a portion of the insert 12 as will be described in greater detail below. The tabs 76 are generally directed towards the axis B and downwardly generally toward the base 50. The lower contact surfaces 80 are positioned to engage the compression insert 12 and hold such insert 12 in a desired position, prohibiting rotation of the insert 12 about the axis B. The tabs 76 are typically initially disposed parallel to the axis B and then a tool (not shown) is inserted into the aperture 68 from outside of the receiver 10 to engage and push the respective tab 76, thereby bending the tab 76 inwardly in a direction toward the axis B until the tab 76 is at a desired angular position, such as is illustrated in FIGS. 76 and 9-11. Such bending of the tabs 76 may be performed either prior to or after assembly of the receiver 10 with the insert 12. It is also foreseen that the tabs 76 may be machined or otherwise pre-fabricated to be angled or directed toward the axis B so as to engage the insert 12 as shown in the drawing figures. The illustrated tabs 76 are resilient, having a spring-like nature. Thus, when operatively cooperating with the insert 12, the tabs 76 bias against the insert 12, holding such insert in a desired position; and yet the tabs 76 are flexible enough to allow a user to make desired minor adjustments of the position of the insert within the receiver 10.

With further reference to FIGS. 6-11, communicating with and located beneath the channel 56 of the receiver 10 is a chamber or cavity, generally 82, defined in part by an internal substantially spherical seating surface 84 and an inner substantially cylindrical surface 86. The cylindrical surface 86 that defines a portion of the cavity 82 opens upwardly into the channel 56. A closure guide and advancement run-out or recess 87 is disposed between the guide and advancement structure 66 and the cylindrical surface 86. The recess 87 is sized and shaped for receiving a flanged portion of the insert 12 as will be described more fully below. The inner substantially spherical surface 84 that is located below the surface 86 is sized and shaped for mating with the shank upper portion 8. However, it is noted that the surface 84 could have other shapes, for example, conical.

The base 50 further includes a restrictive neck 88 defining a bore, generally 90, communicating with the spherical surface 84 of the cavity 82 and also communicating with a lower exterior 92 of the base 60. The bore 90 is coaxially aligned with respect to the rotational axis B of the receiver 10. The neck 88 and associated bore 90 are sized and shaped to be smaller than an outer radial dimension of the shank upper portion 8, so as to form a restriction at the location of the neck 88 relative to the shank upper portion 8 to prohibit the upper portion 8 from passing through the cavity 82 and out to the lower exterior 92 of the receiver 10.

With particular reference to FIGS. 2-8, the lower compression or pressure insert 12 includes a substantially cylindrical body 110 integral with a pair of upstanding arms 112. The body 110 and arms 112 form a generally squared-off U-shaped, open, through-channel 114 defined by a planar bottom seating surface 116 and opposed spaced planar walls 118 that are substantially perpendicular to the seating surface 116. The lower seating surface 116 and the walls 118 are sized and shaped to conform to a width of the connecting member 14 and thus configured to operably snugly engage the member 14 at planar outer surfaces thereof as will be described in greater detail below. The arms 112 disposed on either side of the channel 114 each include a top flanged portion 120, each portion 120 including a top planar surface 122, sized and shaped to engage the closure structure 16 and partially cylindrical outer surfaces 124 sized and shaped to fit within the guide and advancement structure run-out relief 87 of the receiver 10. The cylindrical surfaces 124 are disposed substantially perpendicular to the respective adjacent top surfaces 122. Formed in the planar walls 118 near the top surfaces 122 and extending at an oblique angle into the flanged portions 120 are a pair of opposed recesses or relief surfaces 126. As will be described in greater below, the recesses 126 provide relief for material flow of the connecting member 14 material as shown, for example, in FIGS. 11 and 12. Furthermore, each flange 120 includes a bottom surface 127 disposed substantially parallel to the respective top surface 122 and a recessed surface or groove 128 running at an oblique angle with respect to the respective cylindrical surface 124 removing a portion of the flange 120 at the cylindrical surface 124 and the bottom surface 127. The recessed surface or groove 128 is directed downwardly and inwardly toward the channel 114, being spaced from the top surface 122 and intersecting the bottom surface 127. Each of the surfaces 128 is sized and shaped to receive one of the spring tabs 76 of the receiver 10 and engage such respective tab at the inner lower surface 80 thereof. As will be described more fully below, after each of the tabs 76 spring or snap into the respective recessed surface portion 128, the cylindrical surface 124 located on either side thereof prevents rotation of the insert 12 about the axis B with respect to the receiver 10.

Figure 14:
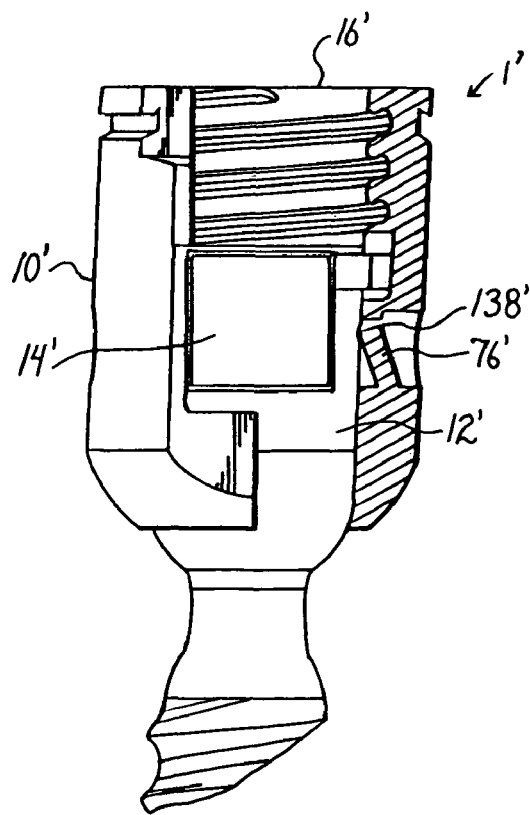
FIG. 14 is an enlarged and partial front elevational view of a second, alternative embodiment of a medical implant assembly according to the invention having a deformable connecting member of rectangular cross-section, with portions broken away to show the detail thereof.

The compression insert 12 further includes a bottom annular surface 130 and a substantially cylindrical outer surface 132. An inner cylindrical surface 134 partially defines a central through-bore extending along a central axis of the compression insert 12. The surface 134 is located between the seating surface 116 and a concave substantially spherical surface 136. The compression insert through-bore is sized and shaped to receive a driving tool (not shown) therethrough that engages the shank drive feature 38 when the shank body 6 is driven into bone. The surface 136 extends between the inner cylindrical surface 134 and the bottom surface 130. The surface 136 is sized and shaped to slidingly and pivotally mate with and ultimately frictionally engage the outer convex spherical surface 34 of the shank upper portion 8. The surface 136 may include a roughening or surface finish to aid in frictional contact between the surface 136 and the surface 34, once a desired angle of articulation of the shank 4 with respect to the receiver 10 is reached. A pair of recesses 138 or flat surfaces are formed in the insert cylindrical surface 132 and located spaced from the flanged portions 120. With reference to FIG. 14, such recesses 138 are sized and shaped to engage spring tabs or other insert holding members as will be described in greater detail below.

The cylindrical surface 132 has an outer diameter slightly smaller than a diameter between crests of the guide and advancement structure 66 of the receiver 10 allowing for top loading of the compression insert 12 with the flanged portions 120 being located between the planar walls 60 during insertion of the insert 12 into the receiver 10 as shown in FIGS. 6 and 7. The receiver is then rotated into place as shown in FIG. 8 with the flanged portions 120 being received in the guide and advancement structure run-out or recess 87. As the insert 12 is rotated into a desired position, the spring tabs 76 snap into the recessed portions 124, and thereafter hold the insert 12 in a desired alignment between the channel 56 of the receiver and the channel 114 of the insert 12. The lower compression insert 12 is sized such that the insert 12 is ultimately received within the cylindrical surface 86 of the receiver 10 below the guide and advancement structure 66 with the flanged top portions 120 received in the recesses 87 formed below the guide and advancement structure 66 and the bottom-surface 130 being spaced from the receiver base. The receiver 10 fully receives the lower compression insert 12 and blocks the structure 12 from spreading or splaying in any direction. It is noted that assembly of the shank 4 within the receiver 10, followed by insertion of the lower compression insert 12 into the receiver 10 are assembly steps typically performed at the factory, advantageously providing a surgeon with a polyaxial bone screw with the lower insert firmly snapped into place and thus ready for insertion into a vertebra.

The compression or pressure insert 12 ultimately seats on the shank upper portion 8 and is disposed substantially in the upper cylindrical portion 86 of the cavity 82, with the tabs 76 engaging the insert 12 at the grooves 128, thereby holding the insert 12 in desired alignment with respect to the connecting member 14. In operation, the insert 12 extends at least partially into the channel 56 such that the seating surface 116 substantially contacts and engages the adjacent planar surface of the connecting member 14 when such member 14 is placed in the receiver 10 and the closure structure or top 18 is tightened therein. The connecting member 14 is held in spaced relation with the lower seat 58 of the receiver 10.

With reference to FIGS. 1 and 10-13, the elongate connecting member 14 illustrated in the drawing figures is a solid elongate bar of rectangular cross-section. More particularly, the illustrated embodiment is solid and has as square cross-section. Thus, the member 14 includes a first pair of opposed planar surfaces 140 and a second pair of equally spaced opposed planar surfaces 142 disposed perpendicular to the surfaces 140. The illustrated member 14 further includes beveled edges and first and second end surfaces 144 and 146. The illustrated connecting member 14 is made from a polymer, in particular, polyetheretherketone (PEEK). The member 14 may be made from a variety of materials including metal, metal alloys or other suitable materials, including, but not limited to plastic polymers such as PEEK, ultra-high-molecular weight-polyethylene (UHMWP), polyurethanes and composites, including composites containing carbon fiber. Furthermore, the connecting member 14 may be a component of a dynamic stabilization connecting member, with the bar or bar portion 14 that is operatively disposed within the insert channel 114 also being integral with or otherwise fixed to a more flexible, bendable or damping component that extends between adjacent pairs of bone screws 3. It is foreseen that as long as the longitudinal connecting member has sufficient viscoelastic behavior, any cross-sectional shape (i.e., square, oval, round, non-round) could be used for the longitudinal connecting member. The channel in the insert could be modified to fit the shape of the longitudinal connecting member. After sufficient pressure is applied to the longitudinal connecting member by the one-piece closure, and plastic deformation occurs, additional pressure by the closure is then directly applied to the compression or pressure insert, thereby securely locking both the longitudinal connecting member and the polyaxial mechanism of the bone anchor.

With reference to FIGS. 1 and 9-11, the closure structure or closure top 16 can be any of a variety of different types of closure structures for use in conjunction with the present invention with suitable mating structure on the upstanding arms 52. In the embodiment shown, the closure top 16 is rotatably received between the spaced arms 52. The illustrated closure structure 16 is substantially cylindrical and includes an outer helically wound guide and advancement structure 152 in the form of a flange form that operably joins with the guide and advancement structure 66 disposed on the arms 52 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 16 downward between the arms 52 and having such a nature as to resist splaying of the arms 52 when the closure structure 16 is advanced into the channel 56. The illustrated closure structure 16 also includes a top surface 154 with an internal drive 156 in the form of an aperture that is illustrated as a hex drive, but may be, for example, a star-shaped internal drive, such as those sold under the trademark TORX or other internal drives, including, but not limited to slotted, tri-wing, spanner, two or more apertures of various shapes, and the like. A driving tool (not shown) sized and shaped for engagement with the internal drive 156 is used for both rotatable engagement and, if needed, disengagement of the closure 16 from the receiver arms 52. It is also foreseen that the closure structure 15 may alternatively include a break-off head designed to allow such a head to break from a base of the closure at a preselected torque, for example, 70 to 140 inch pounds. Such a closure structure would also include a base having an internal drive to be used for closure removal. A bottom surface 158 of the closure is planar, but may include a point, points, a rim or roughening for engagement with the surface 140 of the bar-like connecting member 14. The bottom surface 158 is sized and shaped for engagement with both the connecting member surface 140 and the top planar surfaces 122 of the flanged portions 120 of the insert 12. As will be described in greater detail below, during assembly, the surface 158 first engages the surface 140 of the connecting member. Then, as the closure member 16 is rotated, the surface 158 presses against the surfaces 120, pushing the insert 16 downwardly onto the shank upper portion 8 that in turn presses against the receiver surface 84, locking the shank 4 with respect to the receiver 10 in a desired angular or articulated position. With time, the connecting member 14 may undergo creep or other plastic deformation that may lessen the engagement between the surfaces 140 and 158. However, regardless of any movement of the surface 140, the frictional engagement between the closure member 16 and the insert 12, both preferably made from a metal or metal alloy, such as stainless steel or titanium, will remain rigid and secure.

The closure top 16 may further include a cannulation through bore extending along a central axis thereof and through a surface of the drive 156 and the bottom surface 158. Such a through bore provides a passage through the closure 16 interior for a length of wire (not shown) inserted therein to provide a guide for insertion of the closure top into the receiver arms 52.

With particular reference to FIG. 1, prior to the polyaxial bone screw 3 being placed in use according to the invention, the tip 28 of the shank 6 is inserted into the receiver 10 at the upper opening 57 and then through the bore 88 to a position wherein the shank upper portion 8 is seated on the inner surface 84 of the receiver. Then, with particular reference to FIGS. 6-7, the insert 12 is inserted into the opening 57 with the flanged portions 120 aligned in the channel 56, each flanged portion 120 being located between a pair of opposed planar walls 60 partially defining the channel 56. The insert 12 is then moved downwardly in the channel 56 and toward the cavity 82 as illustrated by the arrow 170 in FIG. 7. As the insert 12 is moved downwardly into the cylindrical portion 86 of the cavity 82, the spring tabs 76 may be pushed outwardly away from the axis A by the flanged portions 120. Once the flanged portions 120 are located below the guide and advancement structure 66 and adjacent the run-out relief 87, the insert 12 is rotated about the axis B of the receiver 10 as illustrated by the arrow 172 in FIG. 8. The flanged portions 120 fit within the relief 87. Once each flanged portion 120 is located centrally with a respective arm 52 of the receiver 10, rotation is ceased and the spring tabs 76 slide or snap into the grooves 128. A slight downward movement of the insert 12 may be needed to fully engage the spring tabs 76 in the grooves with each of the surfaces 80 being biased against the respective groove surfaces 128. The insert 12 is now locked into place inside the receiver 10 with the guide and advancement structure 66 prohibiting upward movement of the insert out of the opening 57 and the spring tabs 76 that are biasing against the insert 12 at the grooves 128 prohibiting rotational movement of the insert 12 with respect to the receiver 10 about the receiver axis B. As illustrated in FIG. 10, the insert 12 seats on the shank upper portion 8 with the surface 136 in sliding engagement with the surface 34. The run-out or relief 87 is sized and shaped to allow for some upward and downward movement of the insert 12 toward and away from the shank upper portion 8 such that the shank 8 is freely pivotable with respect to the receiver 10 until the closure structure 16 presses on the insert 12 that in turn presses upon the upper portion 8 into locking frictional engagement with the receiver 10 at the surface 84.

In use, the bone screw 3 is typically screwed into a bone, such as a vertebra (not shown), by rotation of the shank 4 using a driving tool (not shown) that operably drives and rotates the shank 4 by engagement thereof with the tool engagement structure 38. The vertebra (not shown) may be pre-drilled to minimize stressing the bone and have a guide wire (not shown) that is shaped for the cannula 40 inserted to provide a guide for the placement and angle of the shank 4 with respect to the vertebra. A further tap hole may be made using a tap with the guide wire as a guide. Then, the bone screw 3 is threaded onto the guide wire utilizing the cannulation bore 40 by first threading the wire into the bottom opening 28 and then out of the top at the internal drive 38. The shank 4 is then driven into the vertebra, using the wire as a placement guide.

With reference to FIGS. 10-11, the connecting member 14 is eventually positioned in an open or percutaneous manner within the receiver channel 56 and then into the channel 114 defined by the bottom planar seating surface 116 and the planar walls 118. The member surfaces 140 and 142 are closely received within the planar walls of the insert 12. The closure structure or top 16 is then inserted into and advanced between the arms 52 so as to bias or push against the upper surface 140 of the connecting member 14. Alignment of the planar surfaces 140 and 142 of the connecting member 14 with the squared off U-shaped channel 114 of the insert 14 is initially provided and then maintained by pressure placed on the insert 12 at grooves 128 by the spring tabs 76. The closure structure 16 is rotated, using a tool engaged with the inner drive 156 until a selected pressure is reached at which point the connecting member 14 fully engages the planar surfaces 116 and 118 of the insert 12 and the connecting member 14 is urged toward, but not in contact with the lower seat 58 of the receiver 10 that defines the squared off U-shaped channel 56. As the closure member 16 is rotated and urged downwardly against first the connecting member 14 and then the flanged portions 120 of the insert 12, for example, with a pressure of about 80 to about 120 inch pounds, frictional locking of the shank upper portion 8 against the receiver surface 84 at a desired angle of articulation is accomplished not only by forces transferred through the connecting member 14 but also by direct engagement between the closure member 16 and the insert 12 at the flanged portions 120. Thus, if the connecting member 14 exhibits creep, as would be expected by the PEEK connecting member 14 illustrated in the drawing figures, movement or flow of the member 14 would not diminish the locking frictional engagement between the shank upper portion 8 and the receiver surface 84 as neither the insert 12 nor the receiver 10 (both made from metal such as titanium, for example) would exhibit creep or other deformation. In such an assembly 1, the benefit to the patient of a flexible or dynamic connecting member 14 as well as the benefit of a bone screw 3 having a secure locking mechanism (metal to metal frictional engagement) is accomplished.

If removal of the connecting member 14 from any of the bone screws 3 is necessary, or if it is desired to release the connecting member 14 at a particular location, disassembly is accomplished by using the driving tool (not shown) that mates with the internal drive 156 on the closure structure 16 to rotate and remove the closure structure 16 from the cooperating receiver 10. Disassembly is then accomplished in reverse order to the procedure described previously herein for assembly.

Figure 12:
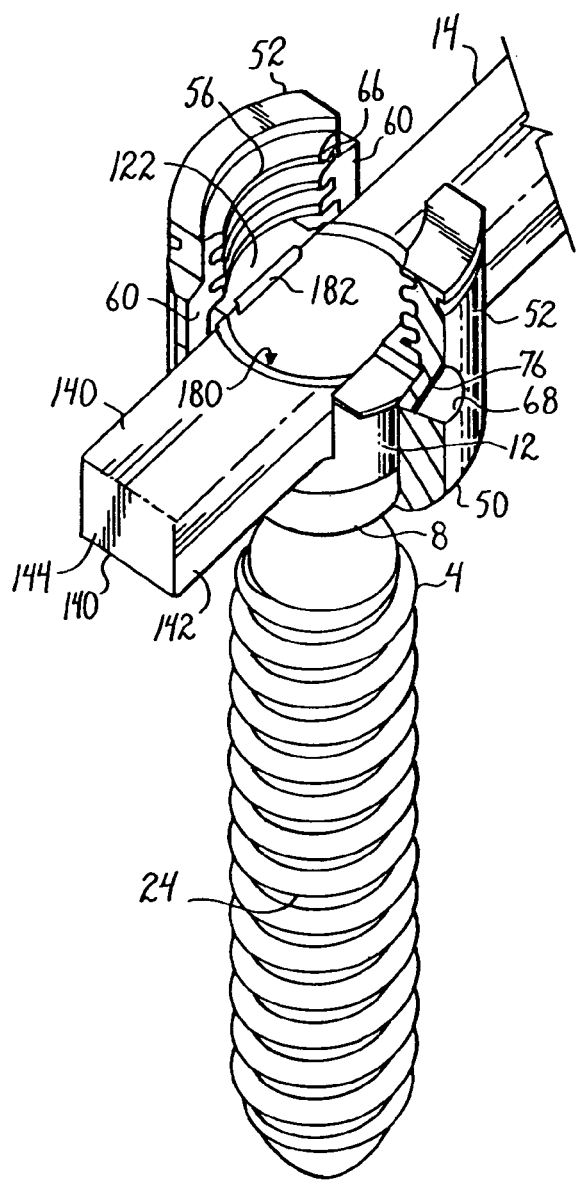
FIG. 12 is an enlarged and partial upper perspective view of the assembly of FIG. 10 but with the closure structure removed to show deformation of the longitudinal connecting member and also shown with other portions broken away to show the detail thereof.

With reference to FIG. 12, there is illustrated an assembly 1 of the invention wherein the closure member 16 has been removed after an amount of time wherein the PEEK connecting member 14 has exhibited some deformation due to creep. It is noted how the member 14 is compressed at the area 180 where the closure structure 16 bottom surface 158 had been pressing on the member upper surface 140. Also illustrated is the flow of connecting member 14 material 182 into the recesses 126 formed in the insert 12. Such material 182 disposed within the recesses 126 advantageously provides further frictional engagement between the insert 12 and the connecting member 14.

Figure 13:
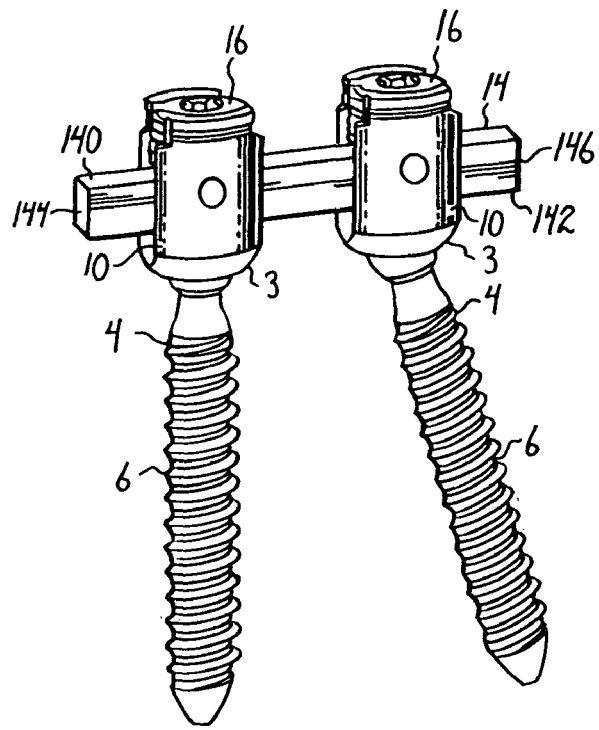
FIG. 13 is a perspective view showing the assembly of FIG. 1 attached to a second polyaxial bone screw of FIG. 1.

With reference to FIG. 13, the connecting member 14 is typically assembled with two or more bone screws 3. The combination of the connecting member 14 with planar surfaces and the bone screw receiver 10 having a channel and insert 12 that includes planar surfaces for closely receiving the member 14 is shown. An advantage of such an assembly is torsional control of the medical implant system. As compared to rigid rods made from metals or metal alloys, a dynamic medical implant 1 of the invention is desirably more flexible in bending or flexing. Furthermore, the combination between a bar-shaped connecting member and receiver with planar surfaces provides stability and strength to withstand torsional forces that, for example, a cylindrical PEEK rod captured by a receiver with a U-shaped channel would not provide. If a more rigid support is eventually required, the bar-shaped member 14 may be replaced by a stiffer cylindrical or bar-shaped rod having a diameter or width the same or similar to the cross-sectional width of the member 14. Such a rod of circular cross-section would be adequately received and closely held between the planar walls 116 and 118 of the insert 14 and the same or similar closure top 16 could be used to hold such a rod in the receiver 10 and also lock the polyaxial mechanism, placing the shank 4 and the receiver 10 in a desired angular relationship with one another.

Figure 15:
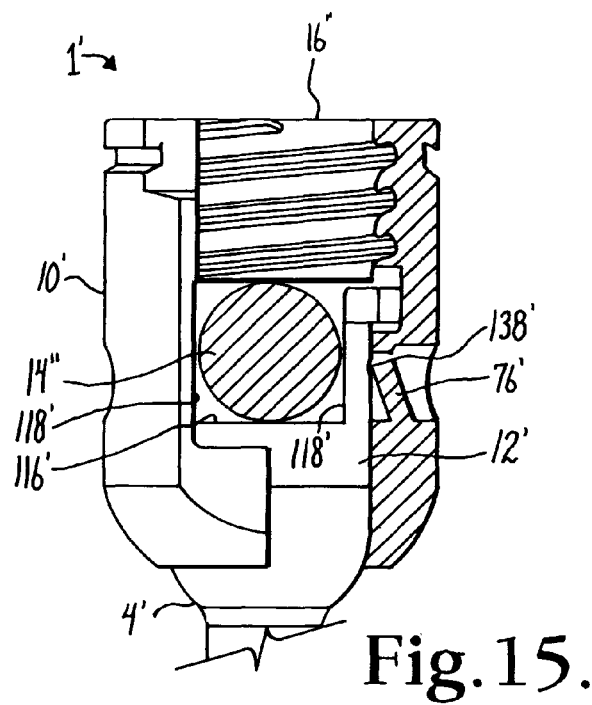
FIG. 15 is an enlarged and partial front elevational view of the embodiment of FIG. 14 with portions broken away to show the detail thereof and further showing replacement of the deformable connecting member with a rigid rod of circular cross-section.

With reference to FIGS. 14 and 15, an alternative assembly 1' is illustrated. The assembly 1' is identical to the assembly 1 previously described herein with the exception of an aspect of a receiver 10' that is otherwise substantially similar to the receiver 10 previously described herein. The assembly 1' therefore includes a shank 4', an insert 12', a connecting member 14' and a closure member 16' that are identical or substantially similar in form and function to the respective shank 4, insert 12, connecting member 14 and closure member 16 previously described herein with respect to the assembly 1. As compared to the spring tabs 76 of the receiver 10 that extend in a downward direction toward the base 50 of the receiver 10, the receiver 10' includes a pair of spring tabs 76' that extend upwardly and toward a closure structure 16'. The spring tabs 76' bias against the insert 12' at recesses 138' identical to the recesses 138 described herein with respect to the insert 12.

With reference to FIG. 15, if a more rigid support is eventually required, the bar-shaped member 14' is shown being replaced by a stiffer cylindrical rod 14" having a diameter equal to the width of the member 14'. As shown in FIG. 15, the rod 14" is received and closely held between planar walls 116' and 118' of the insert 14' and a closure top 16" substantially similar to the closure top 16' abuts against the rod 14" but does not abut against the lower pressure insert 12'. Frictional engagement of the closure top 16" and the rod 14" fixes the rod 14" in the receiver 10' and also locks the polyaxial mechanism, fixedly placing the shank 4' and the receiver 10' in a desired angular relationship with one another.

Figure 16:
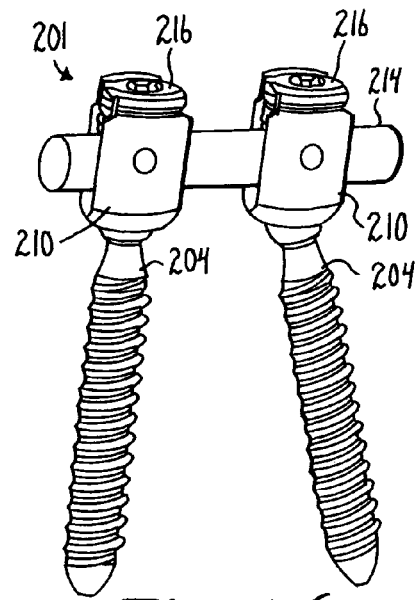
FIG. 16 is a perspective view showing two bone screws of a third, alternative embodiment of a medical implant assembly according to the invention holding a deformable connecting member of circular cross-section.
Figure 17:
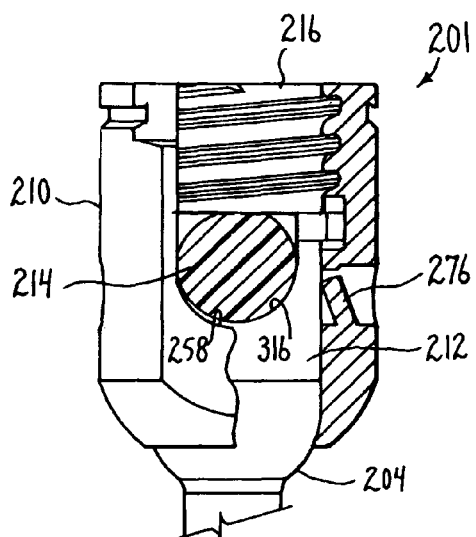
FIG. 17 is an enlarged and partial front elevational view of one of the bone screws and the connecting member of FIG. 16 with portions broken away to show the detail thereof.
Figure 18:
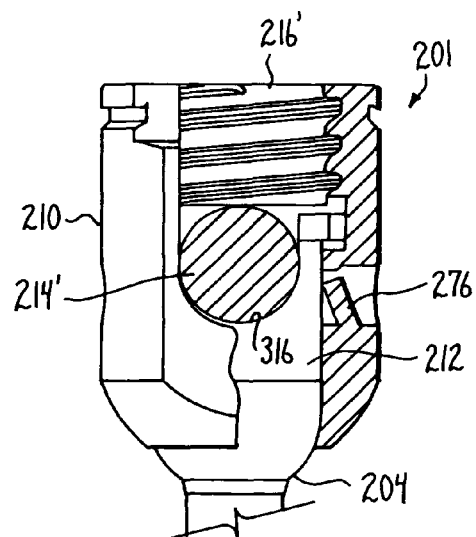
FIG. 18 is an enlarged and partial front elevational view of the embodiment of FIG. 17 with portions broken away to show the detail thereof and further showing replacement of the deformable connecting member with a rigid rod of circular cross-section.

With reference to FIGS. 16-18, another alternative assembly 201 is illustrated. The assembly 201 is identical to the assembly 1' previously described herein with the exception that the bottom planar surfaces of the lower pressure insert and receiver have been replaced by curved surfaces, forming U-shaped channels for holding a connecting member having substantially circular cross-section, such as deformable or rigid rods. The assembly 201 therefore includes a shank 204, a receiver 210, an insert 212, a connecting member 214 and a closure member 216 that are substantially similar in form and function to the respective shank 4, receiver 10, insert 12, connecting member 14 and closure member 16 previously described herein with respect to the assembly 1 with the following exceptions: The receiver 210 includes spring tabs 276 that are identical or substantially similar to the spring tabs 76' of the assembly 1'. Also, a U-shaped surface 258 replaces the planar surface 58 that partially defines the channel 56 of the receiver 10. Similarly, the insert 212 includes a U-shaped surface 316 that replaces the planar bottom surface 116 and portions of the side surfaces 118 of the insert 12. Therefore, the insert 212 and the receiver 210 are sized and shaped to closely receive the connecting member 214 that differs from the connecting member 14 in that the member 214 has a circular cross-section as compared to the rectangular cross-section of the member 14. As best illustrated in FIG. 17, the rod-shaped deformable connecting member 214 is closely held or cradled by the insert 212 surface 316, with the connecting member 214 being held spaced from the receiver surface 258. The closure top 216 presses and deforms the connecting member 214 and also engages the lower pressure insert 212. Engagement between the closure 216 and the insert 212 keeps the bone screw shank 204 in a desired locked position with respect to the receiver 210 even if further deformation of the connecting member 214 occurs that might loosen the connection between the connecting member 214 and the closure top 216.

With reference to FIG. 18, if a more rigid support is eventually required, the deformable rod 214 is shown being replaced by a stiffer cylindrical rod 214'. The more rigid rod 214' is received and closely held by the surface 316 and a closure top 216' substantially similar to the closure top 216 abuts against the rod 214' but does not abut against the lower pressure insert 212. Frictional engagement of the closure top 216' and the rod 214' fixes the rod 214' in the receiver 210 and also locks the polyaxial mechanism, fixedly placing the shank 204 and the receiver 210 in a desired angular relationship with one another.

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having at least one polyaxial bone screw attached to a longitudinal connecting member, the bone screw having a receiver with a channel, the improvement wherein:
   a) at least a portion of the longitudinal connecting member is sized and shaped to be received in the receiver channel; and further comprising:
   b) a compression insert directly engaging both the longitudinal connecting member and a shank of the polyaxial bone screw, the insert having a base, a pair of opposed arms with outer receiver engaging portions, and the opposed arms defining a through channel with a lower connecting member seating surface; wherein
   c) the compression insert is top-loadable in the receiver in a first orientation, wherein, when in the first orientation, the compression insert through channel is substantially perpendicular to the receiver channel, and then rotated to a second orientation, such that the compression insert through channel is substantially parallel to the receiver channel and cooperating receiver portions snap into the receiver engaging portions.

2. The improvement of claim 1 further comprising:
   a) at least one inner recessed relief surface formed in the compression insert, the recessed relief surface receiving material flow of the longitudinal connecting member.

3. The improvement of claim 2 wherein
   a) the at least one recessed relief surface is formed in one of a pair of straight planar side surfaces disposed adjacent to an arm top surface.

4. The improvement of claim 3 wherein
   a) the at least one recessed relief surface is a pair of recessed relief surfaces with one recessed relief surface being formed in each of the pair of planar side surfaces.

5. The improvement of claim 1 wherein
   a) the receiver has an integral alignment structure cooperating with the compression insert, the alignment structure directly engaging the insert and aligning a connecting member receiving channel of the insert with the receiver channel.

6. The improvement of claim 5 wherein
   a) the receiver alignment structure is a first structure that is at least one of a first pressure tab and a first groove; and
   b) the insert having a second structure that is at least one of a second groove cooperating with the first pressure tab and a second pressure tab cooperating with the first groove.

7. The improvement of claim 1 wherein
   a) the compression insert has a first substantially flat planar bottom surface engaging a second substantially flat planar bottom surface of the longitudinal connecting member, the connecting member being made from a polymer and having a substantially flat top planar surface; and further comprising
   b) a one-piece closure structure having a third substantially flat planar bottom surface in direct contact with both the compression insert and the top planar surface of the connecting member.

8. The improvement of claim 7 further comprising at least one recessed relief surface formed in the compression insert, the recessed relief surface receiving material flow of the longitudinal connecting member.

9. The improvement of claim 1 wherein
a) each of the insert arms includes an outer side recess.

10. The improvement of claim 1 wherein
a) the arms form a connecting member receiving channel with a substantially flat planar connecting member seating surface located at the bottom of the connecting member receiving channel.

11. The improvement of claim 10 wherein
a) the receiver engaging portions are outwardly extending flange portions; and
b) when the insert is rotated to the second orientation, each of the flange portions is received in a complementary flange-receiving recess of the receiver such that outer side recesses of the arms directly engage and cooperate with an alignment structure of the receiver.

12. The improvement of claim 11 wherein
a) when the arm outer side recesses directly engage and cooperate with the receiver alignment structure, the insert connecting member receiving channel is aligned with the receiver channel.

13. The improvement of claim 1 wherein
a) the arms are sized and shaped to engage a one-piece integral closure top; and
b) the closure top includes an anti-splay locking structure.

14. The improvement of claim 1 wherein
a) the receiver includes integral spring tab structures sized and shaped to cooperate with the insert so as to block rotation of the insert from the second orientation to the first orientation.

15. The improvement of claim 1 wherein
a) the receiver includes a pair of opposed grooves located, sized and shaped to cooperatively engage respective arm receiver engaging portions when the insert is rotated to the second orientation.

16. The improvement of claim 1 wherein
a) the lower connecting member seating surface is substantially flat.

17. The improvement of claim 1 wherein
a) the lower connecting member seating surface is substantially curved.

18. The improvement of claim 1 wherein
a) the receiver engaging portions of the insert opposed arms are outwardly extending flange portions.

19. The improvement of claim 1 wherein
a) the longitudinal connecting member is deformable.

20. The improvement of claim 1 wherein
a) the compression insert has an insert channel that aligns so as to receive the connecting member with the receiver channel when the compression insert is in the second orientation.

21. The improvement of claim 1 wherein
a) the receiver engaging portions are a pair of opposed outwardly extending portions.

22. In a medical implant assembly having at least one polyaxial bone screw attached to a longitudinal connecting member, the improvement wherein:
a) the connecting member is at least partially deformable; and further comprising:
b) a compression insert engaging directly on the longitudinal connecting member and also engaging directly on a bone screw shank of the polyaxial bone screw, the insert having one of a flat lower planar connecting member seating surface and a lower radiused connecting member seating surface; wherein
c) a receiver having structure cooperating with the compression insert, the structure directly engaging the insert and aligning a connecting member receiving channel of the insert with a through channel of the receiver; and wherein
d) the structure directly engaging the insert is a first structure being at least one of a first pressure tab and a first groove, the insert having a second structure being at least one of a second groove cooperating with the first pressure tab and a second pressure tab cooperating with the first groove.

23. In a polyaxial bone screw having a shank in pivotal relationship with a receiver having a channel for receiving a longitudinal connecting member and a closure top, the improvement comprising:
a) an insert having a base, opposed upwardly extending arms with outwardly extending flanges, each arm having a substantially flat, planar surface for receiving and engaging substantially flat, planar surfaces of the longitudinal connecting member, and at least one outer recessed receiver engaging portion for cooperatively engaging an inwardly biased receiver portion, the insert base being in direct engagement with the bone screw shank and the flanges being in direct engagement with the closure top; wherein
b) the insert is top-loadable in the receiver in a first orientation, wherein the arm planar surfaces are substantially perpendicular to the receiver channel, and then rotatable to a second orientation so as to align the arm planar surfaces with the receiver channel.

24. The improvement of claim 23 further comprising at least one recess formed in the insert adjacent to one of the flanges, the recess receiving material flow of the longitudinal connecting member.

25. The improvement of claim 24 wherein the at least one recess is a pair of opposed recesses, each recess formed near one of the flanges.

26. The improvement of claim 23 further comprising a groove formed in at least one of the flanges, the groove receiving a portion of the bone screw receiver.

27. The improvement of claim 26 wherein the portion of the bone screw receiver is a spring tab.

28. In a polyaxial bone anchor assembly having a closure top, a bone screw shank and a receiving member that receives a pressure insert, and a longitudinal connecting member, the improvement wherein:
a) the closure top is of single piece construction and the closure top directly engages both the longitudinal connecting member and a pair of upright arms of the pressure insert, the pressure insert directly engaging both the connecting member and the bone screw shank;
b) the pressure insert is top-loaded in the receiving member in a first orientation, such that a through channel of the pressure insert is substantially perpendicular to a through channel of the receiving member, and then the pressure insert is rotated to a second orientation so as to position a flange of the upright arms within an inner recess of the receiving member and to thereby align the pressure insert through channel with the receiving member through channel; and wherein
c) a recessed relief surface of the insert receives material flow of a longitudinal connecting member received in the aligned insert and receiver through channels when the closure top engages the received longitudinal connecting member.

29. The improvement of claim 28 wherein the longitudinal connecting member is made from a deformable plastic.

30. In a polyaxial bone screw having a shank in pivotal relationship with a receiver having a channel for receiving a longitudinal connecting member and a closure top, the improvement comprising:
   a) an insert having a base, opposed upwardly extending arms with outwardly extending flanges, and a plurality of substantially flat, planar surfaces for receiving and engaging substantially flat, planar surfaces of the longitudinal connecting member, the insert base being in direct engagement with the bone screw shank and the insert flanges being in direct engagement with the closure top; and
   b) a groove formed in at least one of the insert flanges, the groove receiving a portion of the bone screw receiver, the bone screw receiver being a spring tab; wherein
   c) the insert is top-loadable in the receiver in a first orientation, wherein the insert planar surfaces are substantially perpendicular to the receiver channel, and then rotatable to a second orientation so as to align the insert planar surfaces with the receiver channel.

31. In a medical implant assembly having at least one polyaxial bone screw attached to a longitudinal connecting member, the bone screw having a receiver with a channel, the improvement wherein:
   a) at least a portion of the longitudinal connecting member is sized and shaped to be received in the receiver channel; the assembly further comprising:
   b) a compression insert directly engaging both the longitudinal connecting member and a shank of the polyaxial bone screw, the insert having a base, a pair of opposed arms with receiver engaging portions, a lower connecting member seating surface, and a connecting member receiving channel; wherein
   c) the insert is top-loadable in the receiver in a first orientation, wherein when in the first orientation in insert arms are substantially perpendicular to the receiver channel, and then rotated to a second orientation, such that the insert arms are substantially parallel to the receiver channel;
   d) the receiver has an integral alignment structure cooperating with the insert, the receiver alignment structure directly engaging the insert and aligning the insert connecting member receiving channel with the receiver channel, the receiver alignment structure being a first structure that is at least one of a first pressure tab and a first groove; and
   e) the insert has a second structure that is at least one of a second groove cooperating with the first pressure tab and a second pressure tab cooperating with the first groove.

32. In a medical implant assembly having at least one polyaxial bone screw attached to a longitudinal connecting member, the bone screw having a receiver with a channel, the improvement wherein:
   a) at least a portion of the longitudinal connecting member is sized and shaped to be received in the receiver channel; the assembly further comprising:
   b) a compression insert directly engaging both the longitudinal connecting member and a shank of the polyaxial bone screw, the compression insert having a base, a pair of opposed arms with receiver engaging portions, and a lower connecting member seating surface; wherein
   c) the compression insert is top-loadable in the receiver in a first orientation, wherein when in the first orientation the compression insert arms are substantially perpendicular to the receiver channel, and then rotated to a second orientation, such that the compression insert arms are substantially parallel to the receiver channel; and
   a) the receiver includes integral spring tab structures sized and shaped to cooperate with the compression insert so as to block rotation of the compression insert from the second orientation to the first orientation.

* * * * *

UNITED STATES PATENT AND TRADEMARK OFFICE
CERTIFICATE OF CORRECTION

PATENT NO. : 8,353,932 B2
APPLICATION NO. : 12/229207
DATED : January 15, 2013
INVENTOR(S) : Roger P. Jackson It is certified that error appears in the above-identified patent and that said Letters Patent is hereby corrected as shown below:

In the Claims

Column 17, line 37, in claim 31, delete "in insert" and insert --the insert--, therefor.

Column 18, line 33, in claim 32, delete "a)" and insert --d)--, therefor.

Signed and Sealed this
Second Day of July, 2013

Teresa Stanek Rea
*Acting Director of the United States Patent and Trademark Office*